US012629680B2

(12) United States Patent
Nanduri et al.

(10) Patent No.: US 12,629,680 B2
(45) Date of Patent: May 19, 2026

(54) UNIVERSAL ASSAY CARTRIDGE AND METHODS OF USE

(71) Applicant: Cepheid, Sunnyvale, CA (US)

(72) Inventors: Harika Nanduri, Sunnyvale, CA (US); Andrew Weitsman, Sunnyvale, CA (US); Jennifer Lynn Glass, San Jose, CA (US); Michelle Wei, Sunnyvale, CA (US); Tina Noyes, Sunnyvale, CA (US)

(73) Assignee: Cepheid, Sunnyvale, CA (US)

( * ) Notice: Subject to any disclaimer, the term of this patent is extended or adjusted under 35 U.S.C. 154(b) by 863 days.

(21) Appl. No.: 17/855,578

(22) Filed: Jun. 30, 2022

(65) Prior Publication Data

US 2023/0044516 A1      Feb. 9, 2023

Related U.S. Application Data

(60) Provisional application No. 63/217,672, filed on Jul. 1, 2021.

(51) Int. Cl.
B01L 3/00          (2006.01)
C12Q 1/6844      (2018.01)
(52) U.S. Cl.
CPC ...... B01L 3/502761 (2013.01); C12Q 1/6844 (2013.01); *B01L 2200/04* (2013.01); *B01L 2200/0647* (2013.01); *B01L 2200/16* (2013.01); *B01L 2300/0654* (2013.01); *B01L 2300/0681* (2013.01); *B01L 2300/0864* (2013.01); *B01L 2400/0487* (2013.01); *B01L 2400/0644* (2013.01)

(58) Field of Classification Search
None
See application file for complete search history.

(56) References Cited

U.S. PATENT DOCUMENTS

| | | |
|---|---|---|
| 2003/0162304 A1 | 8/2003 | Dority et al. |
| 2011/0071055 A1* | 3/2011 | Belgrader ......... B01L 3/502715 422/68.1 |
| 2017/0327867 A1* | 11/2017 | Dohale ................... B01L 3/502 |
| 2020/0197934 A1 | 6/2020 | Amshey et al. |

OTHER PUBLICATIONS

International Preliminary Report on Patentability and Written Opinion issued in PCT/US2022/035859, dated Dec. 14, 2023.
International Search Report and Written Opinion issued in PCT/US2022/035859, dated Dec. 9, 2022.

* cited by examiner

*Primary Examiner* — Elizabeth A Robinson
*Assistant Examiner* — Brittany I Fisher
(74) *Attorney, Agent, or Firm* — Merchant & Gould P.C.

(57) ABSTRACT

Sample cartridge, valve assembly and processing methods for providing mechanical lysis, chemical lysis or both for a given fluid sample are provided herein. Such systems can include a sample processing cartridge having a valve assembly configured for transport of the processing of fluid sample within the sample cartridge. The valve assembly can include a valve body and cap that secure a filter therebetween and facilitate inflow of mechanical or chemical lysing agents as needed for a fluid sample. Assay workflows for performing both mechanical and chemical lysis of a fluid sample within the same workflow of a single universal sample cartridge are also provided.

12 Claims, 47 Drawing Sheets

FIG. 2

Valve Cap 50

Valve Body 30

Filter 40

Cart A Valve Body (Cross-sectional view)

Universal  Valve Body (Cross-sectional view)

Close up of filter pocket geometry

Current Cart A valve body

Current Cap Design
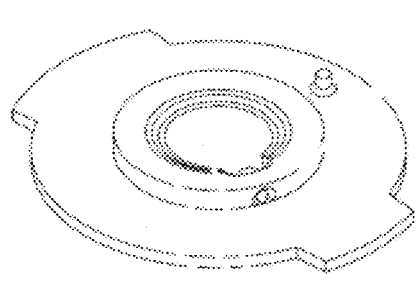
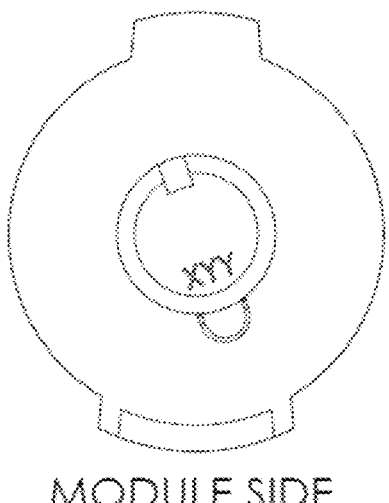
VALVE BODY SIDE
FIG. 10A
MODULE SIDE
FIG. 10B
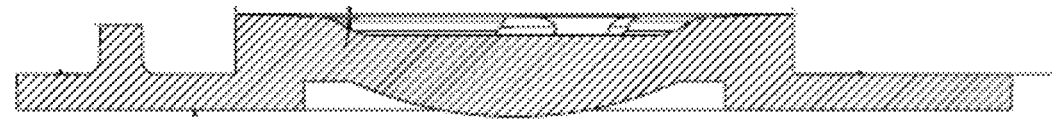
FIG. 10C RCC Valve Body
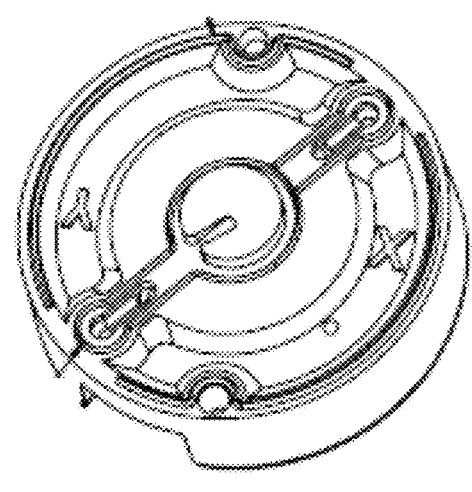
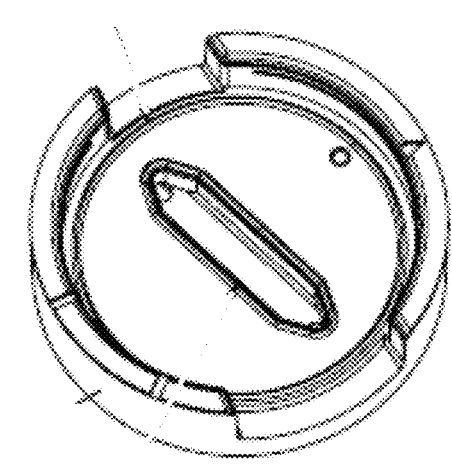
FIG. 11A
FIG. 11B
FCC Cap
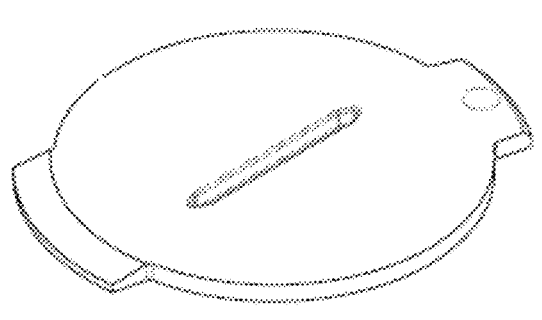
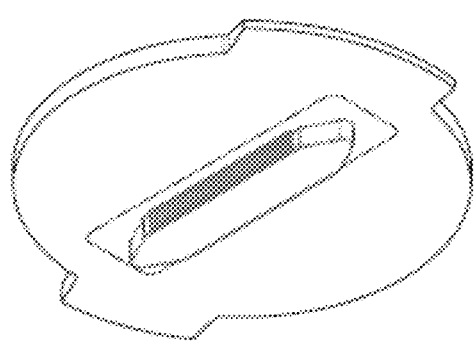
FIG. 11C
FIG. 11D

VALVE BODY SIDE

MODULE SIDE

Filter Gap

No Gap (< .003")

Valve Cap

Filter

Gap (> .003")

Valve Cap

Filter

Supports

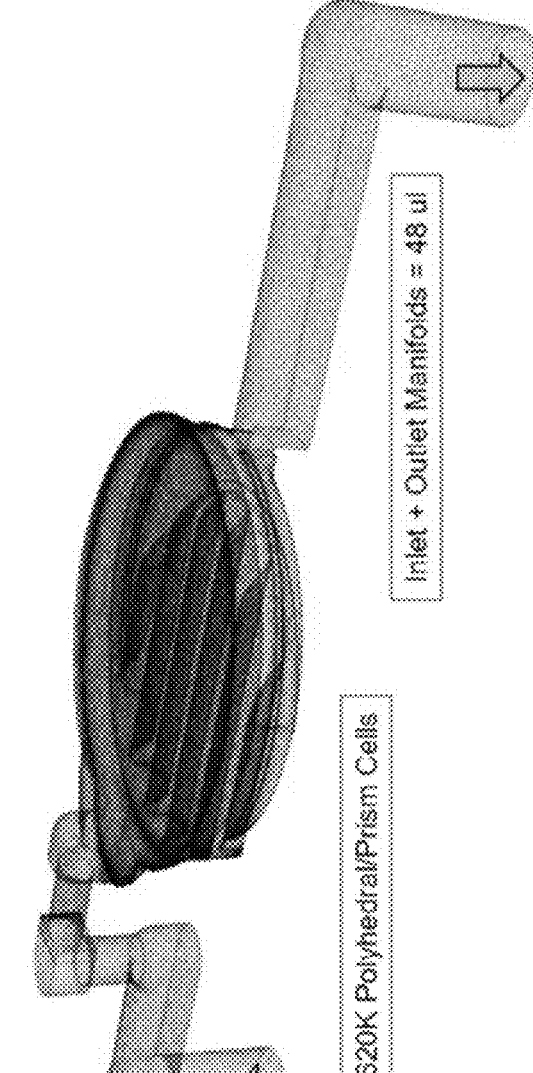

Inlet-Filter-Outlet Model

* The fluid domain analyzed is shown below
* A no-slip boundary condition was used on all walls
* The glass beads and the filter were modeled as porous media
  * The resistance of the porous media was obtained from literature (Appendix).

Simulation process
The fluid domain was originally filled with buffer 1

At t=0, buffer 2 was introduced at the inlet at a rate of 10 uL/sec for 200 uL of total inflow 620K Polyhedral/Prism Cells Inlet + Outlet Manifolds = 48 ul

FIG. 15A

Final Simulation— Mass Fraction Fluid 1

- Four regions where buffer 1 remains:
  - Inlet sharp bend
  - Proximal end of filter (Cap/filter/valve interface)
  - Distal end of cap
  - Valve "slots"

Time 40 (s)

New valve

Final Simulation– Mass Fraction Fluid 1

New valve

Residual Fluids – CFD Analysis

- Comparable wash out and residual buffer

| Valve Body Geometry | Buffer 1 % remaining | Outlet Concentration |
|---|---|---|
| Current Design | 0.28% | 0.15% |
| New Design | 0.38% | 0.28% |

Current Valve Design

New Valve Design

NOTE: Analysis was performed with new valve cap design

CFD
• Under limit of 1% residual buffer

Tolerance Analysis
• All features/dimensions match Cart A Valve Body
• Additional edge of failure testing in progress
  • Focused on increasing the tolerance window on the filter socket depth and/or cap boss height to be >1.001"

| Valve Body Geometry | Buffer 1 % remaining | Outlet Concentration |
|---|---|---|
| Current Design | 0.28% | 0.15% |
| New Design | 0.38% | 0.28% |

UNIVERSAL ASSAY CARTRIDGE AND METHODS OF USE

CROSS-REFERENCES TO RELATED APPLICATIONS

This application is a Non-Provisional of and claims the benefit of priority of U.S. Provisional Application No. 63/217,672, filed Jul. 1, 2021, the entire contents of which are incorporated herein by reference.

BACKGROUND OF THE INVENTION

The present invention relates generally to the field of biochemical analysis, and in particular to sample cartridges for analyzing a fluid sample.

The analysis of fluids such as clinical or environmental fluids generally involves a series of processing steps, which may include chemical, optical, electrical, mechanical, thermal, or acoustical processing of the fluid samples. Whether incorporated into a bench-top instrument, a disposable cartridge, or a combination of the two, such processing typically involves complex fluidic assemblies and processing algorithms.

Conventional systems for processing fluid samples employ a series of chambers each configured for subjecting the fluid sample to a specific processing step. As the fluid sample flows through the system sequentially from chamber to chamber, the fluid sample undergoes the processing steps according to a specific protocol. Because different protocols require different configurations, conventional systems employing such sequential processing arrangements are not versatile or easily adaptable to different protocols.

In recent years, there has been considerable development in the field of biological testing devices that facilitate manipulate a fluid sample within a sample cartridge to prepare the sample for biological testing by polymerase chain reaction (PCR). One notable development in this field is the GeneXpert sample cartridge by Cepheid. The configuration and operation of these types of cartridges can be further understood by referring to U.S. Pat. No. 6,374,684 entitled "Fluid Control and Processing System," and U.S. Pat. No. 8,048,386 entitled "Fluid Processing and Control." While these sample cartridges represent a considerable advancement in the start of the art when developed, as with any precision instrument, there are certain challenges in regard to performance and use of such systems and processes. Moreover, the precise requirements of different target types (e.g. bacterial or viral) typically necessitates the development of specialized devices and cartridges for each type or class of target, such that testing for a panel of differing targets associated with multiple suspected diseases or conditions, multiple samples must be obtained and multiple cartridges utilized, which quickly becomes costly, cumbersome and time-consuming.

Thus, there is a need for sample cartridges that overcome various challenges observed with regard to performance. There is further need for sample cartridges that provide greater versatility in performing assays for range of differing targets. There is further need for such devices that performs a wide range of sample processing steps in a robust and consistent manner and that are compatible with existing technologies to reduce costs and improve patient access.

BRIEF SUMMARY OF THE INVENTION

The present invention pertains to sample cartridge devices and associated components, particularly sample cartridge devices capable of performing sample preparation for various differing types of targets within the same cartridge, as well as associated methods of use.

In one aspect, the invention provides a sample cartridge for separating a desired analyte from the sample and for holding the analyte for chemical reaction and optical detection. The invention also pertains to an instrument module that receives the cartridge for sample processing and operates the cartridge to perform sample preparation and analytical testing. The desired analyte is typically intracellular material (e.g., nucleic acid, proteins, carbohydrates, or lipids). In a preferred use, the analyte is nucleic acid which the cartridge separates from the fluid sample and holds for amplification (e.g., using PCR or an isothermal amplification method) and optical detection.

In another aspect, the invention pertains to a sample cartridge that utilizes a valve body platform that allows for detection of enveloped and free nucleic acid targets. In some embodiments, the valve body includes a sample processing region or lysing chamber that provides for heat, mechanical, and/or chemical lysis. This allows a single cartridge to provide lysing for a multitude of differing types of target, thus, can be considered a "universal assay cartridge." In some embodiments, the sample cartridge can perform processing and detection of both bacterial targets requiring mechanical lysing and viral targets suited for chemical lysing. In some embodiments, the improved valve assembly provides for a sample cartridge capable of combined capture and detection of targets that do not require heat and/or mechanical lysis as well as targets that do require heat and/or mechanical lysis. In some embodiments, such valve assemblies are compatible with existing instrument modules that currently operate conventional sample cartridges directed to only one type of lysing.

In some embodiments, the valve assembly interfaces with the existing cartridge body such that operation of the cartridge by the instrument module is substantially the same or similar as a conventional sample cartridge. In some embodiments, the instrument module includes updates in modified operating instructions to perform workflows of sample preparation that perform multiple operations, such as chemical lysing, heat lysing, and mechanical lysing, of a single fluid sample with the same sample cartridge. In some embodiments, the instrument module reads or obtains the information regarding a panel of assays being performed, then operates according to a workflow that corresponds to one or all of heat lysing, mechanical lysing and chemical lysing depending on the assays being performed.

In another aspect, the invention pertains to a valve assembly that improves performance in regard to any of: consistency of fluid flow and filtering, distribution of forces, and distribution of in-fill (e.g. glass beads) for mechanical lysing. The valve assembly can include additional features that improve upon performance and functionality of the valve assembly as compared to conventional valves assemblies of sample cartridges.

In some embodiments, the valve assembly includes a valve body that interfaces with a valve cap to define an interior sample processing region or lysing chamber therebetween, the valve cap and valve body securing a filter therebetween, a fluid inlet in the valve cap and a fluid outlet in the valve body. In some embodiments, the cap includes a boss feature that interfaces with the valve body and is reduced in height, as compared to the conventional design, so as to accommodate a thicker filter material. In some embodiments, the fluid flow path through the inlets and outlet and lysing chamber or sample processing region have been improved to smooth transitions and eliminate any sharp angles to improve fluid flow therethrough and reduce residual buffer carryover.

In some embodiments, support features are added to the valve cap and valve body within the sample processing region or lysing chamber defined therebetween so as to improve in-fill ability and to reduce filter stress.

In some embodiments, the improvements include utilizing one or more protrusions in the cap adjacent an inlet port so as to increase clearance between any filter and the cap to improve fluid flow of sample and improve flow of in-fill, such as glass beads, for mechanical lysing. The one or more protrusions can include one or more posts on either or both sides of the inlet or outlet ports. In some embodiments, the posts are oval shaped with a major axis extending in a direction of flow. Experimental results using these post features improved yields of in-fill of glass beads within the sample processing region from 70% to 90%.

In other embodiments, the improvements include one or more protrusions or posts extending from the valve body adjacent an outlet so as to improve fluid flow across the filter region by maintaining a suitable gap between the filter and the valve body. This feature can reduce maximum pressure, for example by 5 psi, during assay testing and avoid clogging of the filter. In some embodiments, the posts are oval shaped with a major axis extending in a direction of flow. In some embodiments, the valve body includes a series of ridges extending in the direction of the fluid flow. In embodiments, having one or more posts near the outlet, the ridges extend only partly across the chamber, for example, about ¾ or less across the chamber and the posts are disposed between the series of ridges and the outlet. Experimental results showed that a valve body that included support posts adjacent the outlet reduced filter tears up to 10% by considerably reducing stresses in the filter.

In some embodiments, the valve assembly utilizes filters that are laser cut, which studies have shown to have reduced tears by up to 10%. Conventional approaches typically utilize mechanical cutting means, such as die cutting.

In a preferred embodiment, the cartridge has a sample port for introducing a sample into the cartridge, and a sample flow path extending from the sample port. The cartridge also has a lysing chamber in the sample flow path. The lysing chamber contains at least one filter for capturing cells or viruses from the sample as the sample flows through the lysing chamber. The lysing chamber is defined by at least one wall having an external surface for contacting the transducer to sonicate the lysing chamber. Beads may optionally be disposed in the lysing chamber for rupturing the cells or viruses as the chamber is sonicated. The cartridge can also include a waste chamber in fluid communication with the lysing chamber via the sample flow path for receiving the remaining sample fluid after the sample flows through the lysing chamber. The cartridge can further include a third chamber connected to the lysing chamber via an analyte flow path for receiving the analyte separated from the sample. The third chamber is preferably a reaction chamber for chemically reacting and optically detecting the analyte. The cartridge also includes at least one flow controller (e.g., valves) for directing the sample into the waste chamber after the sample flows through the lysing chamber and for directing the analyte separated from the sample into the third chamber. The design of the cartridge permits the efficient processing of large sample volumes to enable the accurate detection of low concentration analytes.

In some embodiments, the sample cartridge employs a rotary valve configuration that allows fluidic communication between a fluid processing region selectively with a plurality of chambers including, for example, a sample chamber, a waste chamber, a wash chamber, a lysis chamber, and a mastermix or reagent chamber. The fluid flow among the fluid processing region and the chambers is controlled by adjusting the position of the rotary valve. In this way, the metering and distribution of fluids in the apparatus can be varied depending on the specific protocol.

In accordance with some aspects of the present invention, a fluid control and processing system comprises a housing having a plurality of chambers, and a valve body including a first fluid processing region continuously coupled fluidicly with a fluid displacement region. The fluid displacement region is depressurizable to draw fluid into the fluid displacement region and pressurizable to expel fluid from the fluid displacement region. The valve body includes a plurality of external ports. The first fluid processing region is fluidicly coupled with at least two of the external ports. The fluid displacement region is fluidicly coupled with at least one of the external ports of the valve body. The valve body is adjustable with respect to the housing to allow the external ports to be placed selectively in fluidic communication with the plurality of chambers. At least one of the plurality of chambers is a processing chamber including at least one port for selectively communicating with at least one of the external ports of the valve body. The processing chamber provides an additional fluid processing region.

In some embodiments, at least one of the fluid processing regions in the valve body or in the processing chamber contains a fluid processing material which is an enrichment material or a depletion material. The fluid processing material may comprise at least one solid phase material. The solid phase material may comprise at least one of beads, fibers, membranes, filter paper, glass wool, polymers, cellulose fibers, and gels. In some embodiments, the filter is formed of glass fibers to facilitate affinity binding with the nucleic acids. In some embodiments, the filter has a nominal pore size of 0.2 to 2 um, preferably 0.5 to 1 um, typically about 0.7 um. In some embodiments, the cartridge includes glass beads for mechanical lysing, the glass beads having a nominal diameter of about 200 um or less, typically about 100 um. In some embodiments, the filter is a glass fiber disk without acrylic binder. In some embodiments, the filter material has a nominal thickness between 400 um and 450 um, typically about 420 um. In some embodiments, the cut filter is anywhere between 0.375"-0.400" in diameter, with the nominal diameter being around 0.385" or 9779 um. The fluid processing material may comprise a filter and beads, and in some embodiments comprises at least two types of beads. In some embodiments, a single type of solid phase material is used to perform at least two different functions which are selected from the group consisting of cell capture, cell lysis, binding of analyte, and binding of unwanted material. In some embodiments, the processing chamber includes a receiving area for receiving a processing module containing an enrichment material or a depletion material. In a specific embodiment, at least one of the chambers is a reagent chamber containing dried or lyophilized reagents. In some embodiments, the fluid processing material comprises at least one liquid phase material, such as ficoll, dextran, polyethylene glycol, and sucrose. The fluid processing material is contained in the fluid processing region by one or more frits. In a specific embodiment, the external ports are disposed on a generally planar external port surface of the valve body.

In some embodiments, the filter materials (e.g. glass beads, glass fibers) can be chemically treated to enhance performance. In some embodiment, the filter materials are chemically treated to improve binding and/or separation for isolation and purification of nucleic acids from nucleic-acid containing samples passed through the filter material. In some embodiments, the chemical treatment can include bonding of a compound to the filter material. In some embodiments, the compound comprises a DNA binding ligand, such as an amino-containing compound and can be used as a separating material for nucleic acid isolation. Particularly, the DNA binding ligand on the surface of the glass support provides high nucleic acid binding capacity for isolating the nucleic acid from a sample. In some embodiments, the compound is chemically bonded to the glass material via a linker, such as by an oligoethylene linker or a PEG oligomer. Suitable chemical treatments are described in U.S. Provisional Application No. 63/337,014 filed Apr. 29, 2022, entitled "Nucleic Acid Extraction and Isolation with Heat Labile Silanes and Chemically Modified Solid Supports," the entire contents of which are incorporated herein by reference for all purposes. In some embodiments, the glass filter materials (e.g. glass fibers, beads) can be reacted with a silanizing group to obtain the separating materials disclosed herein. Accordingly, the silanol groups of the glass fibers can be reacted with compounds represented by the formula Y-(L)y-SiX3, wherein each X is independently selected from halogen, alkoxy, dialkylamino, trifluoromethanesulfonate, or a straight, branched, or cyclic alkyl; L is an optional linker such as an alkylene, heteroalkylene linker group, cyanuric chloride, an alkylamine, or a combination thereof and which may be optionally substituted; and Y is a DNA binding ligand, as described herein. The reaction of glass fibers with the compounds described herein provides in glass fibers surface DNA binding groups. The DNA binding ligand or the substituent Y can comprise a plurality of amine groups; a plurality of amide groups; or a combination thereof. For example, the DNA binding ligand or Y can comprise at least two, at least three, at least four, at least five, at least six amine or amide groups, or a combination thereof. In some embodiments, the DNA binding ligand or Y comprises an alkylamine group, an imidazole group, or a combination thereof. Representative examples of the amine group include spermine, methylamine, ethylamine, propylamine, ethylenediamine, diethylene triamine, 1,3-dimethyldipropyl-enediamine, 3-(2-aminoethyl)aminopropyl, (2-aminoethyl) trimethylammonium hydrochloride, tris (2-aminoethyl)amine, or a combination thereof. In some embodiments, the filter materials can comprise aminopropyl (AP) coated glass fiber filters (AP-GFF), glass beads, glass filter fibers, or other suitable solid support or fiber materials known to persons of skill in the art.

In accordance with another aspect of the invention, a fluid control and processing system comprises a housing having a plurality of chambers, and a valve body including a fluid processing region continuously coupled fluidicly with a fluid displacement region. The fluid displacement region is depressurizable to draw fluid into the fluid displacement region and pressurizable to expel fluid from the fluid displacement region. The valve body includes at least one external port, the fluid processing region is fluidicly coupled with at least one external port, and the fluid displacement region is fluidicly coupled with at least one external port of the valve body. The valve body is adjustable with respect to the housing to allow the at least one external port to be placed selectively in fluidic communication with the plurality of chambers.

In some embodiments, the sample cartridge employs a rotary valve configuration to control fluidic movement within the cartridge that allows for selective fluidic communication between a fluid sample processing region and a plurality of chambers in the cartridge. Non-limiting exemplary chambers can include, a sample chamber, a reagent chamber, a waste chamber, a wash chamber, a lysate chamber, an amplification chamber, and a reaction chamber. The fluid flow among the fluid sample processing region and the chambers is controlled by adjusting the position of the rotary valve. In this way, the metering and distribution of fluids in the cartridge can be varied depending on the specific protocol, which allows sample preparation to be adaptable to different protocols such as may be associated with a particular sample type for different types of analysis or different types of samples. For example, the sample cartridge can include a means for cell lysis, e.g., a sonication means so that bacteria and cells in a fluid sample to be analyzed can be lysed. Additional lysis means suitable for use with the instant invention are well known to persons of skill in the art, and can include, chemical lysis, mechanical lysis, and thermal lysis. In some embodiments, the sample includes bacteria, eukaryotic cells, prokaryotic cells, parasites, or viral particles.

In some embodiments, sample processing comprises sample processing steps that are performed from initial sample preparation steps, intermediate processing steps, and further processing steps to facilitate a detection of a target analyte in the biological sample with an attached reaction vessel. For example, sample processing can include preliminary preparation steps, such as filtering, grinding, mincing, concentrating, trapping debris or purifying a rough sample, or steps for fragmenting of DNA or RNA of the target analyte, such as by sonication or other mechanical or chemical means. Sample processing can include various intermediate processing steps, such as filtering, chromatography, or further processing of nucleic acids in the sample, including but not limited to chromatography, bisulfite treatment, reverse transcription, amplification, hybridization, ligation, or fragmentation of DNA or RNA. Sample processing may further include final processing steps, such as final amplification, hybridization, sequencing, chromatographic analysis, filtering and mixing with reagents for a reaction to detect the target analyte, which detection can include optical, chemical and/or electrical detection. While the sample cartridge typically performs analytical testing in an attached reaction tube or reaction vessel, it is appreciated that the sample cartridge can utilize various other means as well (e.g. semiconductor chip).

In some embodiments, the sample processing device can be a fluid control and processing system for controlling fluid flow among a plurality of chambers within a cartridge, the cartridge comprising a housing including a valve body having a fluid sample processing region continuously coupled fluidically with a fluid displacement chamber. The fluid displacement chamber is depressurizable to draw fluid into the fluid displacement chamber and pressurizable to expel fluid from the fluid displacement chamber. The fluid sample processing region includes a plurality of fluid transfer ports each fluidically coupled with one of a plurality of external ports of the valve body. The fluid displacement chamber is fluidically coupled with at least one of the external ports. The valve body is adjustable with respect to the plurality of chambers within the housing to allow the external ports to be placed selectively in fluidic communication with the plurality of chambers. In some embodiments, the valve body is adjustable with respect to the housing having multiple chambers, to place one external port at a time in fluidic communication with one of the chambers.

In some embodiments of the cartridge, the fluid sample processing region can be disposed between the fluid displacement chamber and at least one fluid transfer port. The term "fluid processing region" refers to a region in which a fluid sample is subject to processing including, without limitation, chemical, optical, electrical, mechanical, thermal, or acoustical processing. For example, chemical processing may include a chemical treatment, a change in pH, or an enzymatic treatment; optical processing may include exposure to UV or IR light; electrical processing may include electroporation, electrophoresis, or isoelectric focusing; mechanical processing may include mixing, filtering, pressurization, grinding or cell disruption; thermal processing may include heating or cooling from ambient temperature; and acoustical processing may include the use of ultrasound (e.g. ultrasonic lysis). In some embodiments, the fluid processing region may include an active member, such as a filter, to facilitate processing of the fluid. Additional active members suitable for use with the instant invention are well known to persons of skill in the art. In some embodiments, an energy transmitting member is operatively coupled with the fluid sample processing region for transmitting energy thereto to process fluid contained therein. In some embodiments, the valve body includes a crossover channel, and the valve body is adjustable with respect to the plurality of chambers to place the crossover channel in fluidic communication with two of the chambers concurrently.

The cartridge housing includes one or more branches that extend to one or more transfer ports to which a reaction vessel can be attached so as to facilitate transfer of fluid sample from a chamber of the cartridge into the reaction vessel. In some embodiments, the reaction vessel extends from the housing of the cartridge. These aspects can be understood further by referring to U.S. Pat. No. 8,048,386. It is understood that fluid may flow in either direction into or out of the transfer ports in various embodiments fluid flow is not limited in any particular direction. For example, in an embodiment having a pair of transfer ports, air may be pumped into or evacuated from one of the pair of transfer ports to facilitate flow of the fluid sample into a conduit of the reaction vessel through the fluid transfer port.

In some embodiments, methods for processing an unprepared sample can include steps of: receiving a sample cartridge in a cartridge receiver of a module, the sample cartridge including a biological fluid sample to be analyzed, a plurality of processing chambers fluidically interconnected by a moveable valve body; receiving an electronic instruction to process the biological sample into a prepared sample from the module; performing a sample preparation method in the sample cartridge to process the biological fluid sample into the prepared sample; transporting the prepared sample into a reaction vessel fluidically coupled with the sample cartridge; and performing analysis of the biological fluid sample within the reaction vessel. In some embodiments, transporting the sample may include steps of: moving a cartridge interface unit to move the valve body to change fluidic interconnections between the plurality of sample processing chambers; applying pressure to a pressure interface unit to move fluid between the plurality of processing chambers according to position of the valve body; and fluidically moving the prepared sample into the reaction vessel. Performing analysis of the fluid sample within the reaction vessel with the module. Any result of the analysis can be obtained by the module and communicated to various other devices as desired. In some embodiments, the sample cartridge can be coupled to various other diagnostic components, such as a silicon chip, or may transport the prepared fluid sample to other external diagnostic equipment.

BRIEF DESCRIPTION OF THE DRAWINGS

FIG. 2 illustrates ultrasonic mechanical lysing techniques as performed by one type of conventional sample cartridge and chemical lysing techniques, as performed by conventional sample cartridges, both techniques can be performed by a universal sample cartridge in accordance with some embodiments.

FIGS. 10A-10C illustrate various views of a valve cap of a conventional sample cartridge utilizing mechanical lysing.

FIGS. 11A-11B illustrate various views of a valve body of a conventional sample cartridge utilizing chemical lysing.

FIGS. 11C-11D illustrate various views of a valve cap of a conventional sample cartridge utilizing chemical lysing.

FIG. 15A-15K illustrate various models of washflow analysis for a valve assembly of a universal sample cartridge, in accordance with some embodiments.

DETAILED DESCRIPTION OF THE INVENTION

The present invention relates generally to a system, device and methods for fluid sample manipulation and analysis, in particular, sample cartridges that facilitate processing and analytical testing of biological samples.

I. System Overview

In one aspect, the invention pertains to a sample cartridge that utilizes a valve body platform that allows for detection of enveloped and free nucleic acid targets. In some embodiments, the valve body includes a sample processing region or lysing chamber that provides for either or both mechanical and chemical lysis. This allows a single cartridge to provide lysing for a multitude of differing types of target, thus, can be considered a "universal assay cartridge." In some embodiments, the sample cartridge can perform processing and detection of both bacterial targets requiring mechanical lysing and viral targets suited for chemical lysing.

The sample cartridge device can be any device configured to perform one or more process steps relating to preparation and/or analysis of a biological fluid sample according to any of the methods described herein. In some embodiments, the sample cartridge device is configured to perform at least sample preparation. The sample cartridge can further be configured to perform additional processes, such as detection of a target nucleic acid in a nucleic acid amplification test (NAAT), e.g., Polymerase Chain Reaction (PCR) assay, by use of a reaction tube attached to the sample cartridge. In some embodiments, the reaction tube extends from the body of the cartridge. Preparation of a fluid sample generally involves a series of processing steps, which can include chemical, electrical, mechanical, thermal, optical or acoustical processing steps according to a specific protocol. Such steps can be used to perform various sample preparation functions, such as cell capture, cell lysis, binding of analyte, and binding of unwanted material.

Figure 1:
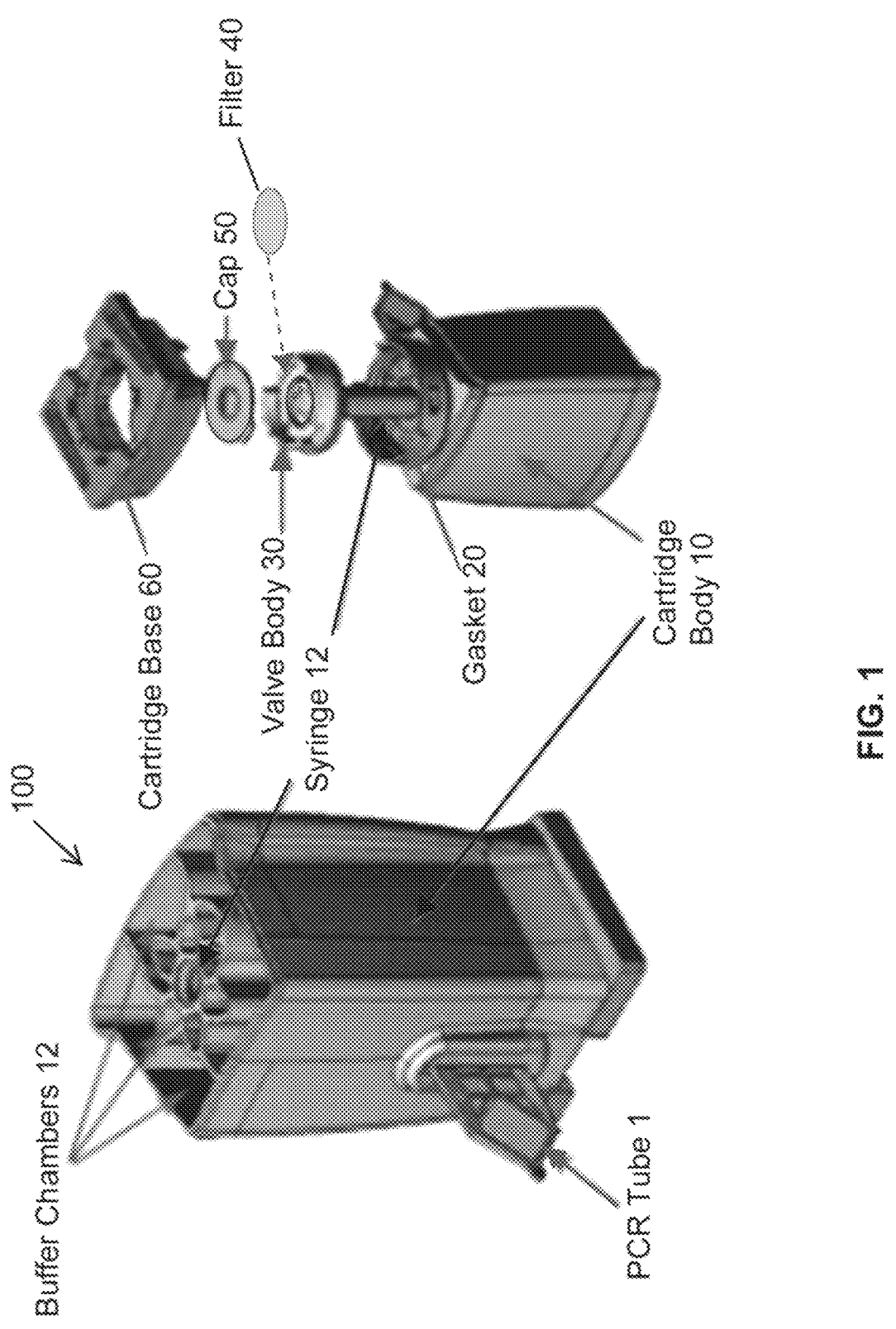
FIG. 1 is an overview of a sample cartridge with a valve assembly having a valve, filter and valve cap, configured for performing differing sample processes, including both chemical and mechanical lysing of targets, in accordance with some embodiments of the invention.

A sample cartridge suitable for use with the invention, includes one or more transfer ports through which the prepared fluid sample can be transported into an attached reaction vessel for analysis. FIG. 1 illustrates an exemplary universal sample cartridge 100 suitable for sample preparation and analytics testing by PCR when received in an instrument module in accordance with some embodiments. The sample cartridge is attached with a reaction vessel 1 ("PCR tube") adapted for analysis of a fluid sample processed within the sample cartridge 100. In some embodiments the reaction tube extends form the cartridge body. Such a sample cartridge 100 includes various components including a main housing 10 having one or more chambers for processing of the fluid sample, which typically include sample preparation before analysis. The instrument module facilitates the processing steps needed to perform sample preparation and the prepared sample is transported through one of a pair of transfer ports into fluid conduit of the reaction vessel 1 attached to the housing of the sample cartridge 100. The prepared biological fluid sample is then transported into a chamber of the reaction tube 1 where the biological fluid sample 4 undergoes nucleic acid amplification. In some embodiments, the amplification is a polymerase chain reaction. In some embodiments, concurrent with the amplification of the biological fluid sample, an excitation means and an optical detection means of the module is used to detect optical emissions that indicate the presence or absence of a target nucleic acid analyte of interest, e.g., a bacteria, a virus, a pathogen, a toxin, or other target analyte. It is appreciated that such a reaction vessel could include various differing chambers, conduits, or micro-well arrays for use in detecting the target analyte. In some embodiments, the reaction tube can comprise multiple separate reaction chambers isolated from each other for the detection of different analytes. In some embodiments, the reaction tube can comprise 2, 3, 4, 5, 6, 7, 8, 9, 10 or more separate isolated reaction chambers. The sample cartridge can be provided with means to perform preparation of the biological fluid sample before transport into the reaction vessel. Any chemical reagent required for viral or cell lysis, or means for binding or detecting an analyte of interest (e.g. reagent beads) can be contained within one or more chambers of the sample cartridge, and as such can be used for sample preparation.

An exemplary use of a reaction vessel for analyzing a biological fluid sample is described in commonly assigned U.S. Pat. No. 6,818,185, entitled "Cartridge for Conducting a Chemical Reaction," filed May 30, 2000, the entire contents of which are incorporated herein by reference for all purposes. Examples of the sample cartridge and associated module are shown and described in U.S. Pat. No. 6,374,684, entitled "Fluid Control and Processing System" filed Aug. 25, 2000, and U.S. Pat. No. 8,048,386, entitled "Fluid Processing and Control," filed Feb. 25, 2002, incorporated herein by reference in their entirety for all purposes.

Various aspects of the sample cartridge 100 can be further understood by referring to U.S. Pat. No. 6,374,684, which described certain aspects of a sample cartridge in greater detail. Such sample cartridges can include a fluid control mechanism, such as a rotary fluid control valve, that is connected to the chambers of the sample cartridge. Rotation of the rotary fluid control valve permits fluidic communication between chambers and the valve so as to control flow of a biological fluid sample deposited in the cartridge into different chambers in which various reagents can be provided according to a particular protocol as needed to prepare the biological fluid sample for analysis. To operate the rotary valve, the cartridge processing module comprises a motor such as a stepper motor that is typically coupled to a drive train that engages with a feature of the valve in the sample cartridge to control movement of the valve in coordination with movement of the syringe, thereby resulting movement of the fluid sample according to the desired sample preparation protocol. The fluid metering and distribution function of the rotary valve according to a particular sample preparation protocol is demonstrated in U.S. Pat. No. 6,374,684.

II. Example Universal Assay Cartridge and Valve Assemblies

A. Overview

FIG. 1 illustrates a universal sample cartridge device 100 fluidically coupled with a reaction vessel 1. The fluid sample cartridge 100 is adapted for insertion into a bay of a module having an instrument interface configured to perform one or more processing steps on a fluid sample contained within the fluid sample cartridge through manipulation of the fluid sample cartridge. The processing steps can include any steps associated with sample preparation, transport of fluid sample, and analytical testing. An instrument interface of the module is incorporated into the module within the bay in which cartridge 100 is received. At right, an exploded view of the sample cartridge assembly is shown, which includes the cartridge body 10, gasket 20, syringe 12, valve body 30, filter 40, valve cap 50 and cartridge base 60. While the basic function of these components may be similar to those of conventional sample cartridges, the valve assembly has been modified to considerably improve performance and to perform multiple types of sample preparation (e.g. mechanical and chemical lysing) with the same sample that would otherwise not be possible with conventional cartridges.

B. Examples Assays for Universal Assay Cartridges

Figure 2:
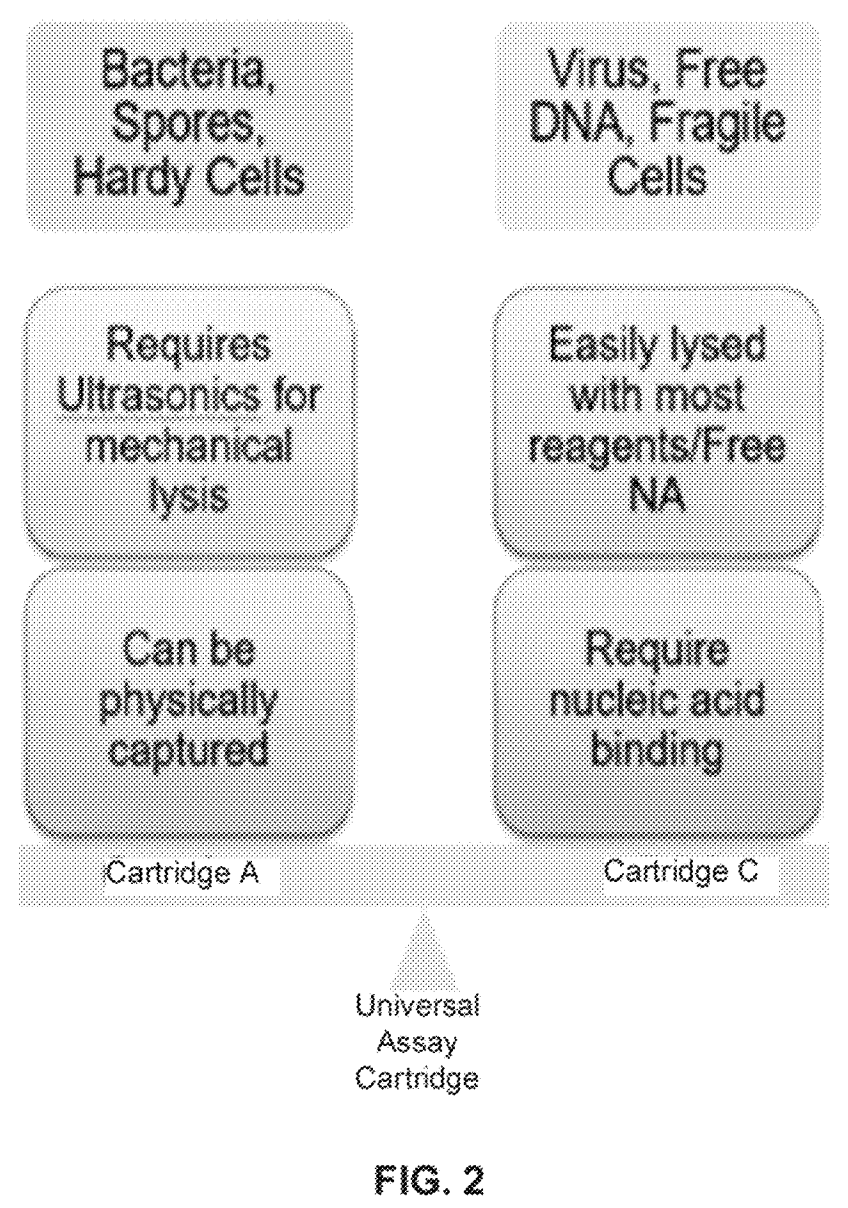

In one aspect, the universal sample cartridge described herein can perform sample preparation and analytical testing for assays that are currently performed by conventional sample cartridges. For example, as shown in FIG. 2, one conventional sample cartridge (Cartridge A) is configured to perform analytical detections for targets including bacteria, spores, and hardy cells, which require mechanical lysis (e.g. ultrasonics, sonication) so that the released nucleic acids can be physically captured and detected. Another conventional sample cartridge (Cartridge C) is configured to perform analytical detections for target including virus, free DNA, and fragile cells, which can be easily lysed with chemical reagents to release the nucleic acids. Typically, these cartridges utilize nucleic acid binding. Currently, the capabilities of each sample configuration are such that each can only perform sample preparation for those designated targets. Advantageously, the universal sample cartridge described herein can perform both of these sample preparation tasks, individually, sequentially or in combination, such that the sample cartridge can replace the conventional cartridges as well as perform complicated assay panels that would otherwise not be achievable with a single sample cartridge.

For example, the universal sample cartridge can be used for the simultaneous detection of the major viral, parasitic and bacterial causes of undifferentiated febrile illness (UFI) in a Tropical Fever Assay panel, all of which can be performed by a sample cartridge utilizing the improved valve assembly described herein. Lysis requirements of possible target organisms responsible for UFI include both viral targets that require chemical lysis, parasitic and bacterial targets may require mechanical lysis. An example of such a test is shown in the table below.

TABLE 1

| Tropical Fever Test | | |
| --- | --- | --- |
| Target Organism | Target Type | Lysis |
| Zika virus | Viral (RNA) | Chemical |
| Dengue virus (serotypes 1-4, undifferentiated) | Viral (RNA) | Chemical |

TABLE 1-continued

| Tropical Fever Test | | |
| --- | --- | --- |
| Target Organism | Target Type | Lysis |
| Chikungunya virus | Viral (RNA) | Chemical |
| P. vivax, P. malariae, P. knowlesi and P. ovale (undifferentiated) | Parasitic | Mechanical/Chemical* |
| P. falciparum | Parasitic | Mechanical/Chemical* |
| Leptospira | Bacterial | Mechanical/Chemical* |
| Salmonella Typhi | Bacterial | Mechanical/Chemical* |

*Dependency on mechanical lysis for optimal detection to be evaluated during Xpert Tropical Fever Test Technical Feasibility Feasibility Additional multi-target assay panels that can be developed for use with the universal sample cartridge may include a Gastrointestinal (GI) Panel, Breast Cancer Panel, and Bacterial Agents or any mixed-target panel. As shown, the differing targets within a single panel can include any of viral targets, fungal targets, parasitic targets, and bacterial targets, or any combination thereof.

C. Example Valve Assemblies

Figure 3:
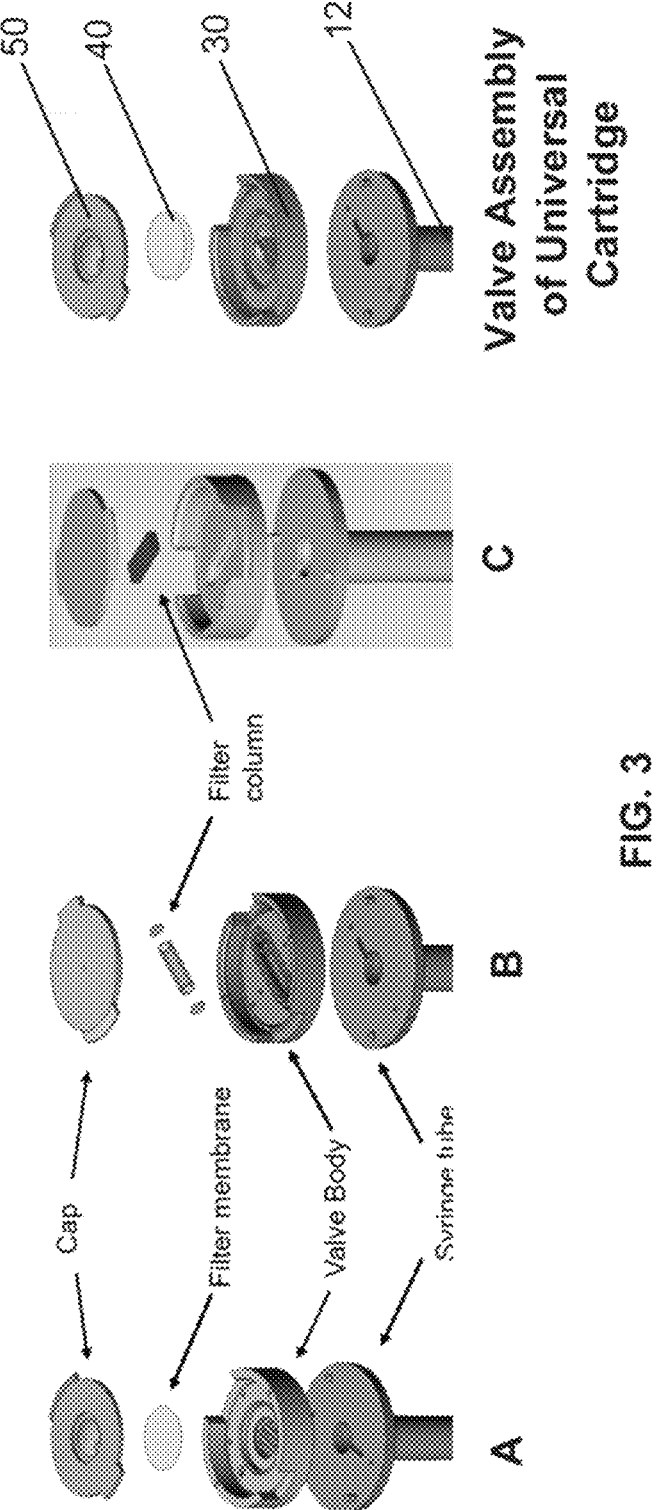
FIG. 3 illustrates a comparison of valve assemblies of conventional sample cartridges A, B, C, each suited for a single type of target lysing as compared to a universal valve assembly for a universal sample cartridge capable of processing multiple differing types of assays requiring different types of lysing.

FIG. 3 illustrates a valve assembly of a universal sample cartridge, in accordance with aspects of the invention, as compared to valve assemblies in conventional cartridge (A, B, C). Cartridge A performs only mechanical lysing for more hardy targets, and Cartridges B and C perform only chemical lysing for viruses, free NA or more fragile targets. In all such cartridges, the valve assembly includes the syringe tube 12, valve body 30, and valve cap 50. In one aspect, the additional capabilities of the valve assembly of the universal sample cartridge rely in part on the filter, features of the valve body and cap, as well as the particular workflow sequence performed by the instrument interface of the module.

Figure 4:
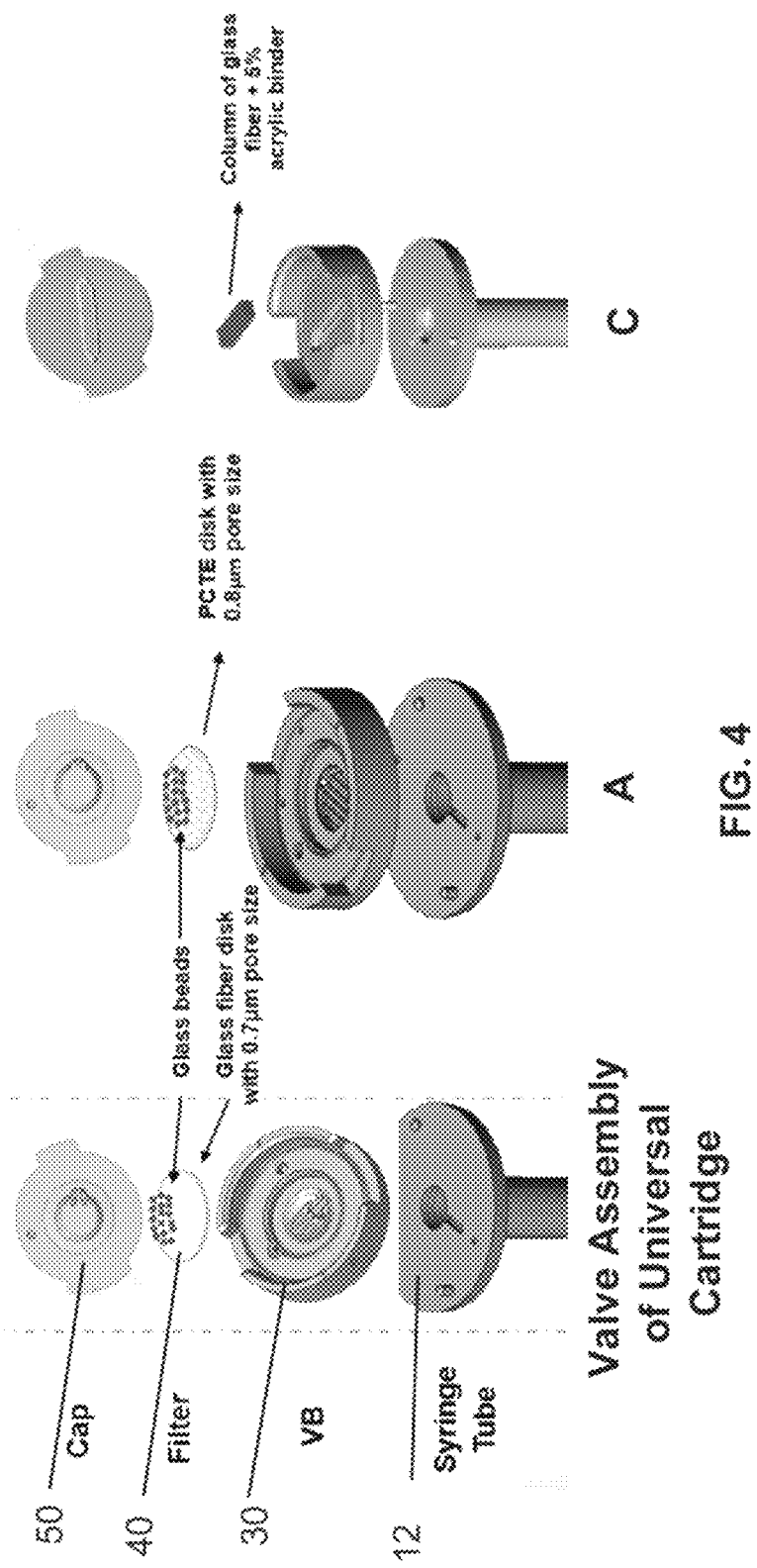
FIG. 4 illustrates a universal valve assembly, in accordance with some embodiments, that utilizes glass beads suited for mechanical lyses of certain types of targets, as compared to conventional valve assemblies in conventional sample cartridges.

In some embodiments, the filter is configured to accommodate glass beads to further facilitate mechanical lysis of hardy targets, as shown in FIG. 4. In this embodiment, the filter 40 is formed of glass fibers and has a 0.7 um pore size. In contrast, Cartridge A utilizes a filter formed as a disk of a polymer film (i.e., PCTE), which while suitable for mechanical lysing, but not suited for chemical lysing. By utilizing a filter having a pore size of 0.7 um, the filter is suitable for receiving suitably sized glass beads for mechanical lysing. Utilizing glass fibers to form the filter facilitates affinity bonding with the free nucleic acid released by chemical lysing. Thus, this filter is suited for both mechanical and chemical lysing.

Figures 5A, 5B, 5C:
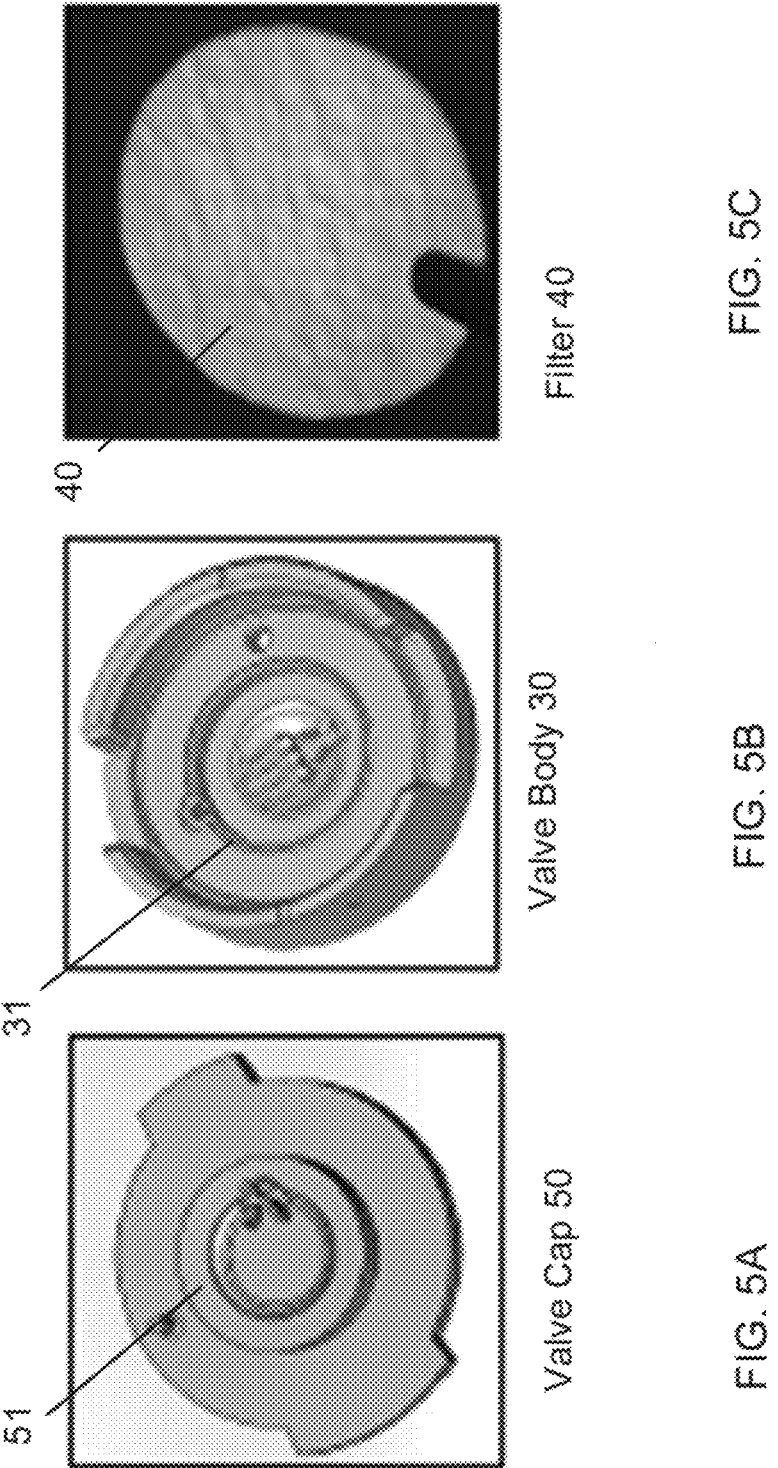
FIGS. 5A-5C illustrates the components of a valve assembly, in accordance with some embodiments.
Figures 6A, 6B, 7A, 7B:
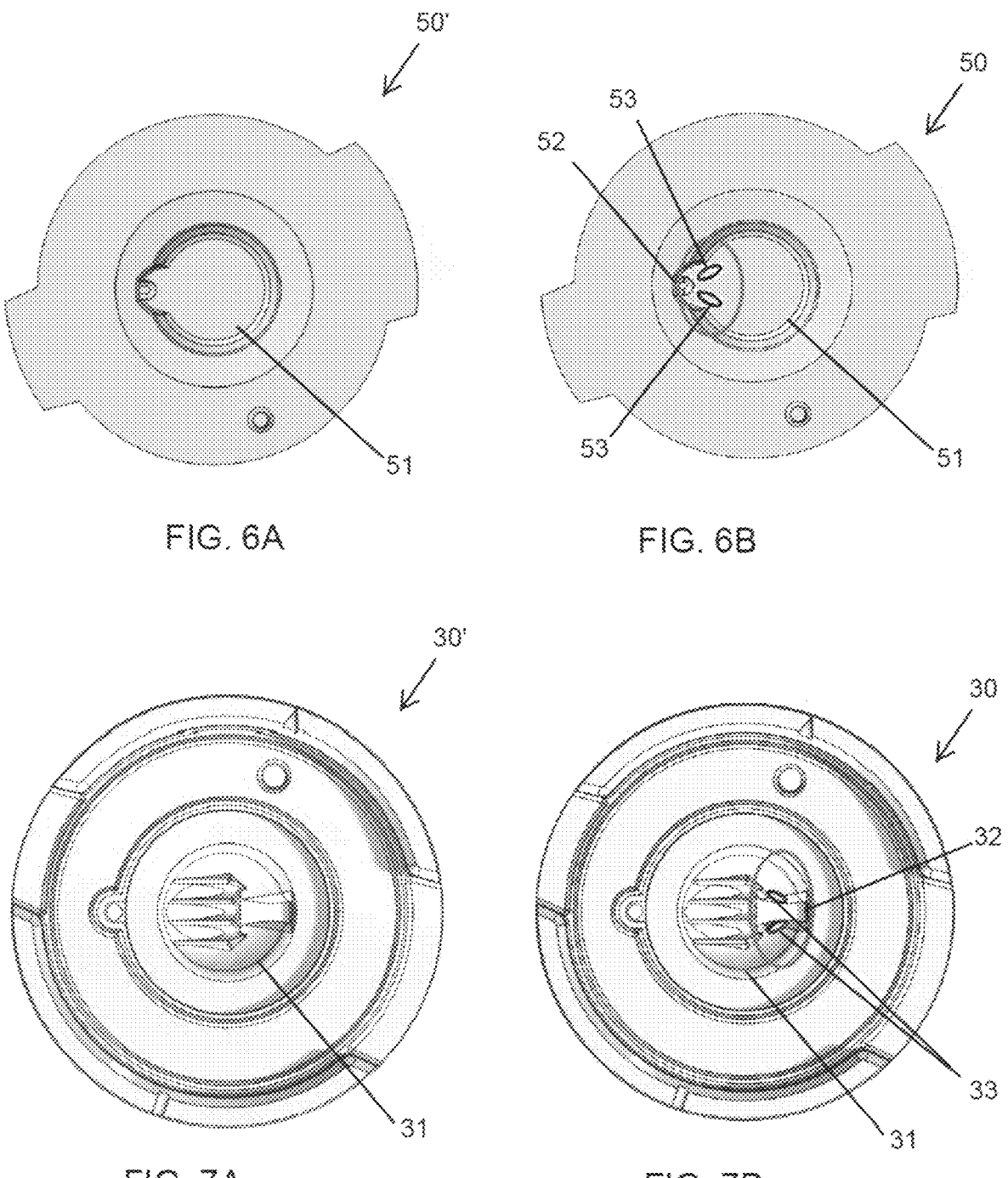
FIGS. 6A-6B compare a valve cap in accordance with some embodiments, as compared with a conventional design.
FIGS. 7A-7B compare a valve body in accordance with some embodiments, as compared with a conventional design.

FIGS. 5A-5C illustrate the valve cap 50, valve body 30 and filter 40 of a valve assembly of a universal sample cartridge, in accordance with some embodiments. The valve cap 50 and valve body 30 include interlocking portions on their peripheries that engage with each so that interior circular regions interface to form a sample processing region or lysing chamber. The cap and valve body include interior circular regions 31, 51 that interface to form an interior sample processing region or lysing chamber. The filter 40 is sized to be secure between the valve cap and valve body FIGS. 6A-6B illustrate valve caps in accordance with some embodiments. FIG. 6A shows a valve cap 50' in accordance with some embodiments, and FIG. 6B shows a valve cap 50 of a similar design that further includes a pair of posts. As shown, the valve caps include an interior circular region 51 that defines the lysing chamber when interfaced with the valve body and a fluidic inlet 52 through which fluid sample and any glass bead infill enters the lysing chamber. In the design of FIG. 6B, the valve cap further includes a pair of protrusions or posts 53, which presses the filter away from the inlet so as to improve consistency of glass infill across the filter so as to improve mechanical lysing.

FIGS. 7A-7B illustrate valve bodies in accordance with some embodiments. FIG. 7A shows a valve body 30' in accordance with some embodiments, and FIG. 7B shows a valve cap 30 of a similar design that further includes a pair of posts. As shown, the valve bodies includes the interior circular region 31 that defines the lysing chamber when interfaced with the valve cap and a fluidic outlet 32 through which fluid sample exits the lysing chamber. In the design of FIG. 7B, the valve body further includes a pair of protrusions or posts 33, which inhibits deflection of the filter toward the outlet so as to reduce pressure peaks on the filter and reduce tearing.

Figure 8A:
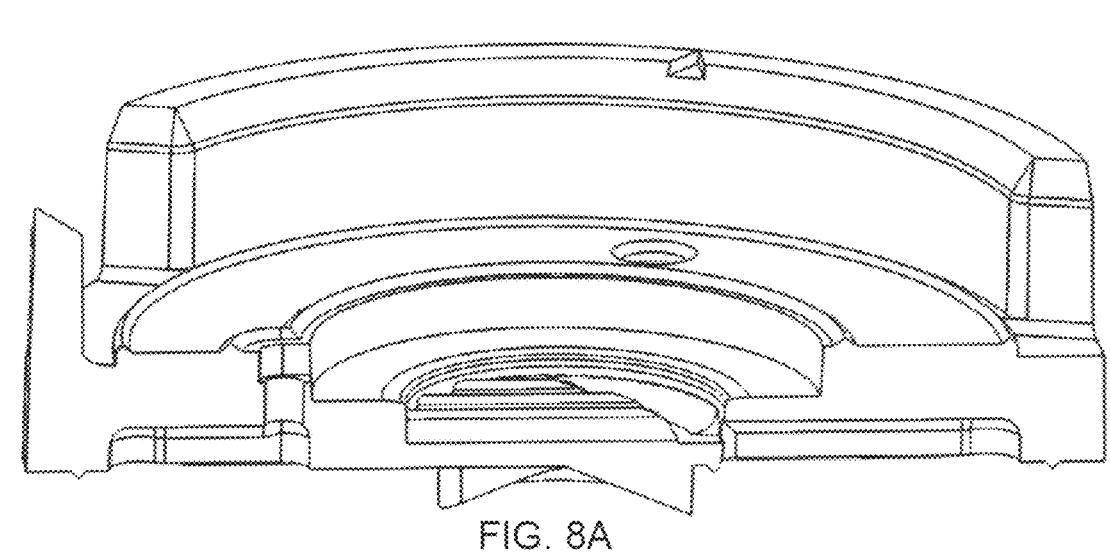
FIGS. 8A-8B illustrate detail views of the filter pocket, as compared with a conventional design.
Figure 8B:
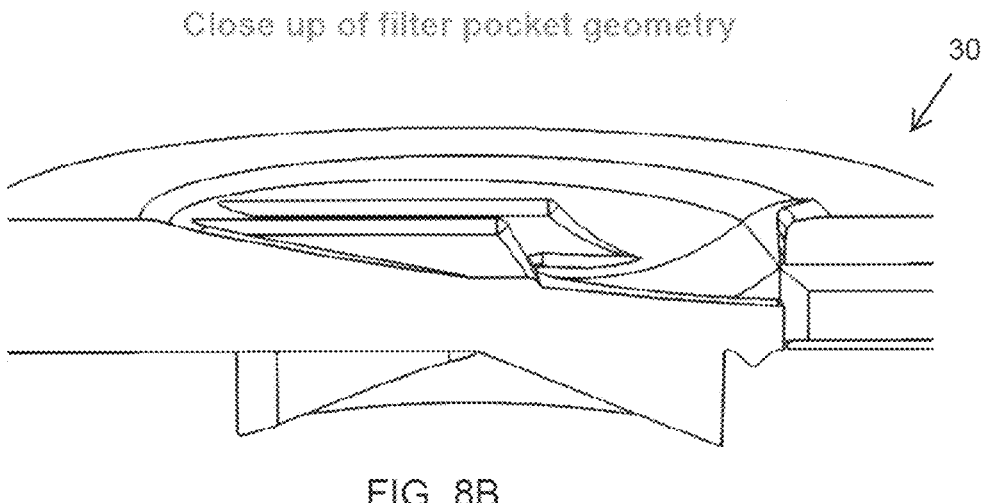
Figure 9A:
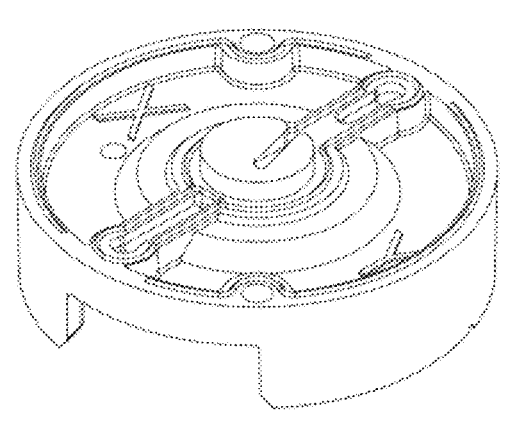
FIGS. 9A-9E illustrate various views of a valve body of a conventional sample cartridge utilizing mechanical lysing.
Figure 9B:
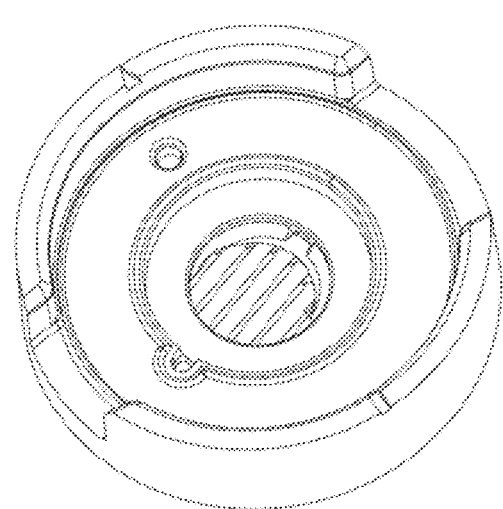
Figure 9C:
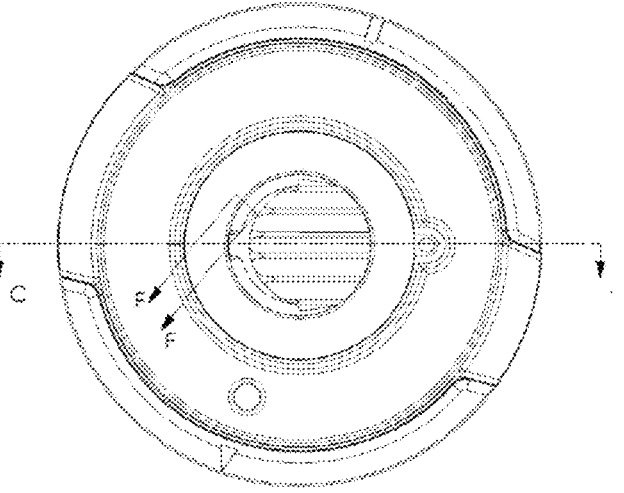
Figure 9D:
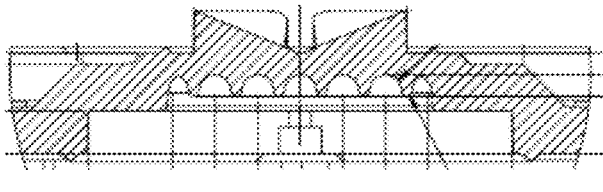
Figure 9E:
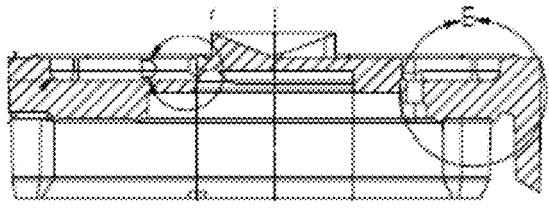
Figure 12A:
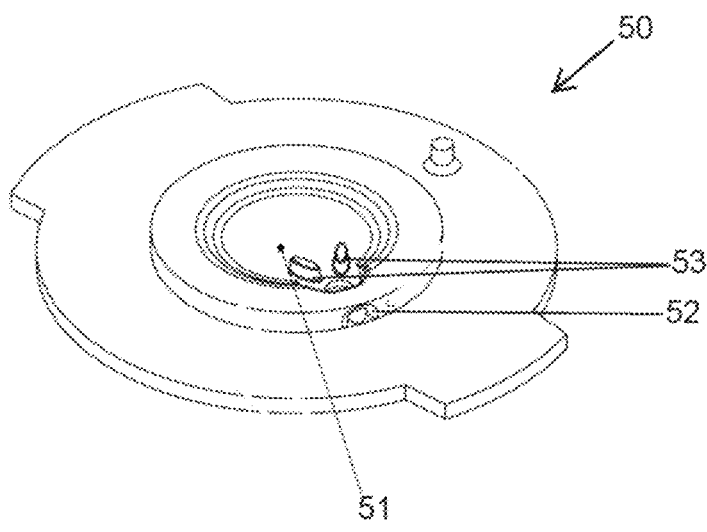
FIGS. 12A-12D illustrate various views of a valve cap of a universal sample cartridge, in accordance with some embodiments.
Figure 12B:
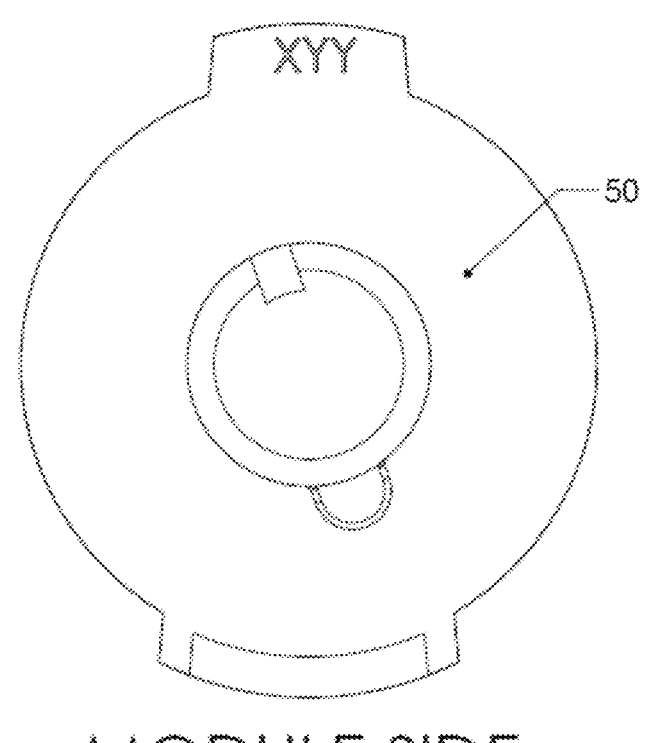
Figure 12C:
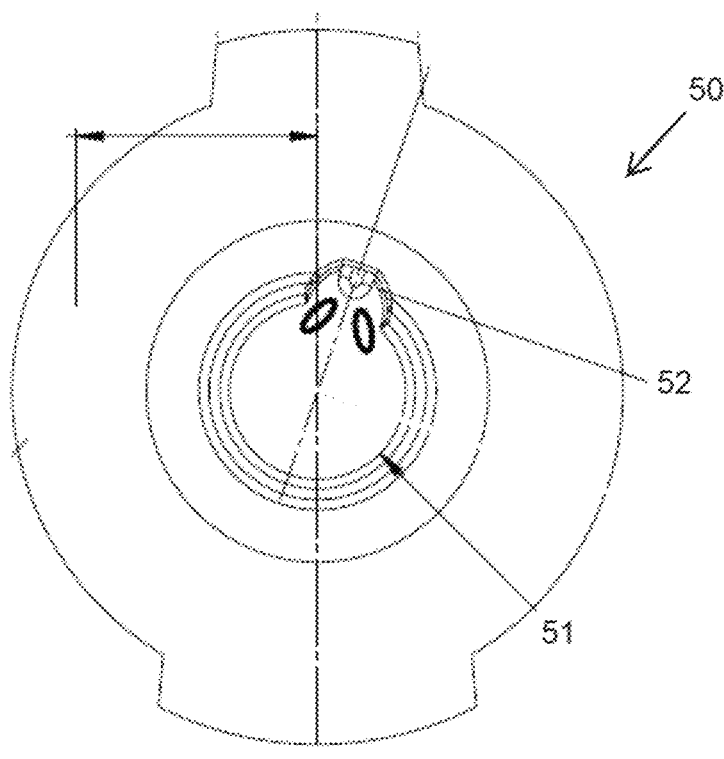
Figure 12D:
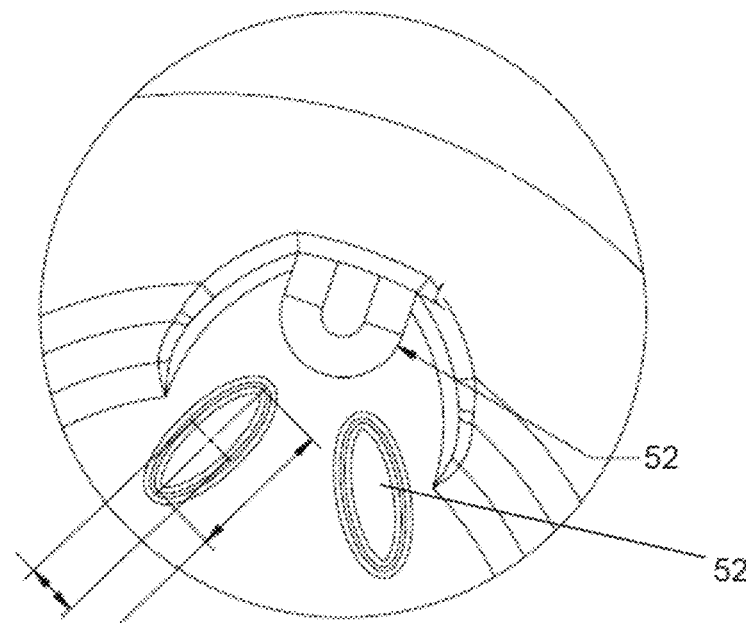
Figure 13A:
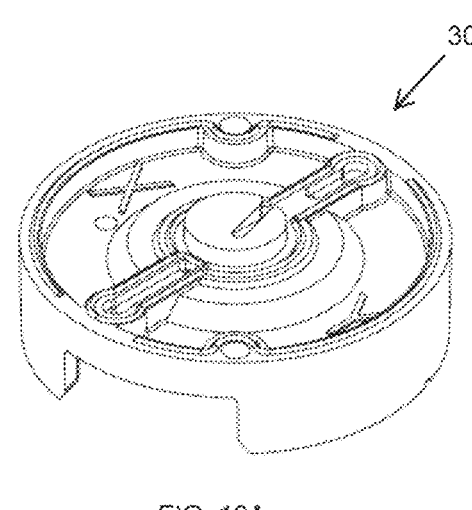
FIGS. 13A-13D illustrate various views of a valve body of a universal sample cartridge, in accordance with some embodiments.
Figure 13B:
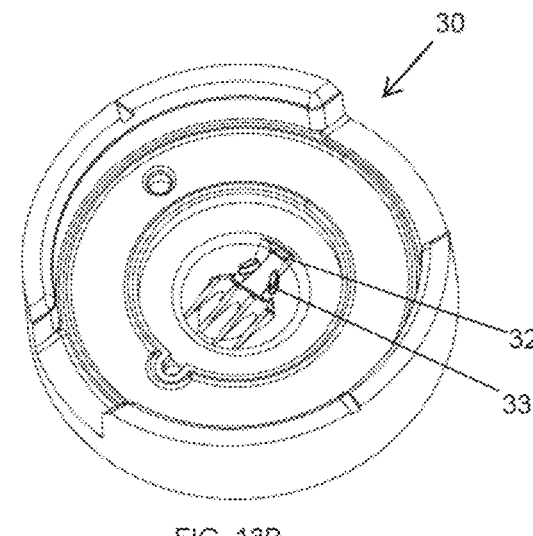
Figure 13C:
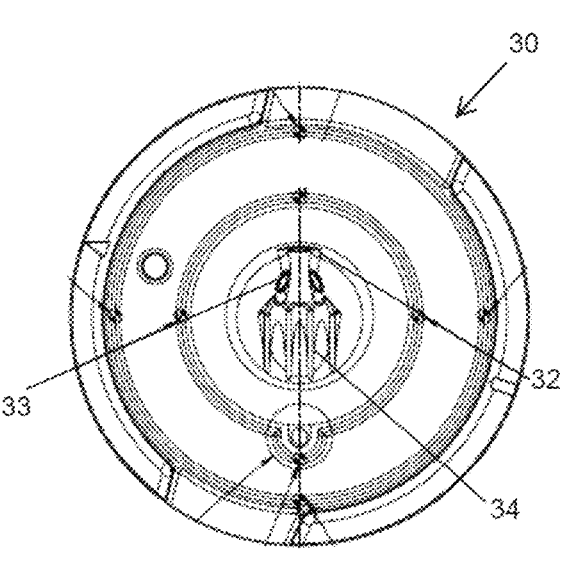
Figure 13D:
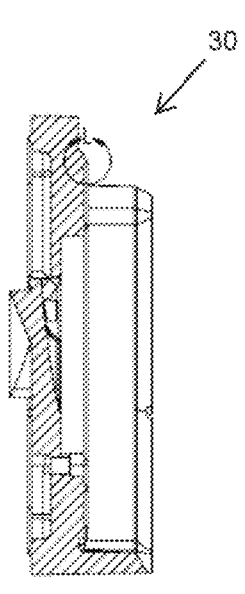

FIGS. 8A and 8B illustrate cross-sectional views of a valve body of a conventional valve assembly (FIG. 8A) and a valve body of an improved valve assembly (FIG. 8B) in accordance with some embodiments. As can be seen, the edges of the chamber or filter pocket have been smoothed such that sharp edges are eliminated, which reduces uneven flow and pressure distributions through the chamber and promote uniform flow through the lysing chamber.

FIGS. 9A-9E illustrate various views of a valve body of a conventional sample cartridge utilizing mechanical lysing and FIGS. 10A-10C illustrate various views of a valve cap of a conventional sample cartridge utilizing mechanical lysing, for comparison with the improved valve assemblies described herein.

FIGS. 11A-11B illustrate various views of a valve body of a conventional sample cartridge utilizing chemical lysing, and FIGS. 11C-11D illustrate various views of a valve cap of a conventional sample cartridge utilizing chemical lysing, for comparison with the improved valve assembly described herein.

FIGS. 12A-12D illustrate various views of a valve cap 50 for a universal sample cartridge, in accordance with some embodiments. The two posts 53 can be seen adjacent the inlet 52. FIGS. 13A-13D illustrate various views of a valve body 30 for a universal sample cartridge, in accordance with some embodiments. The two posts 33 can be seen adjacent the outlet 32 and a series of support ridges 34 support the filter upstream of the outlet.

Figure 14A:
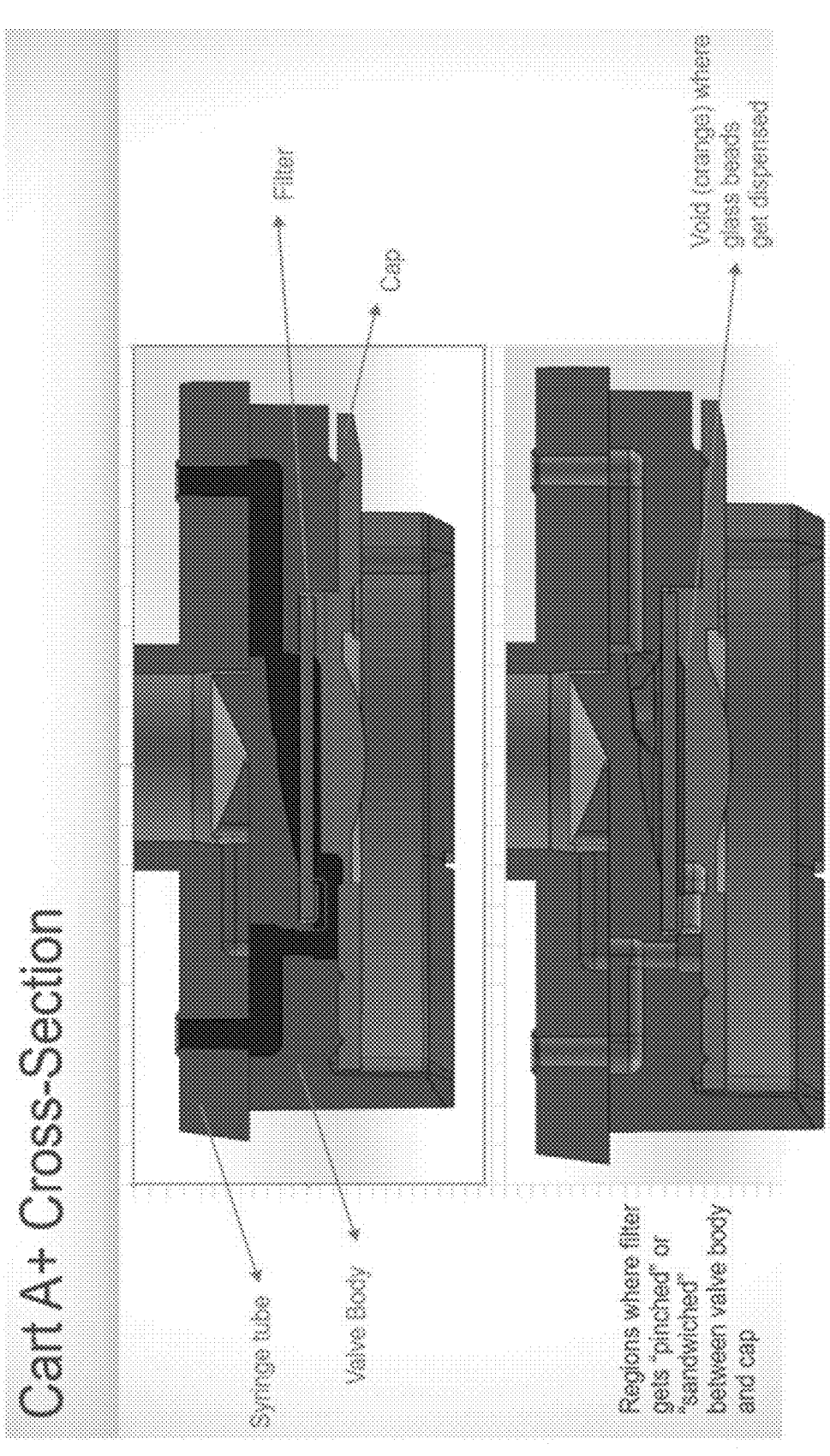
FIG. 14A illustrate cross-sectional views of a valve assembly in accordance with some embodiments.
Figure 14B:
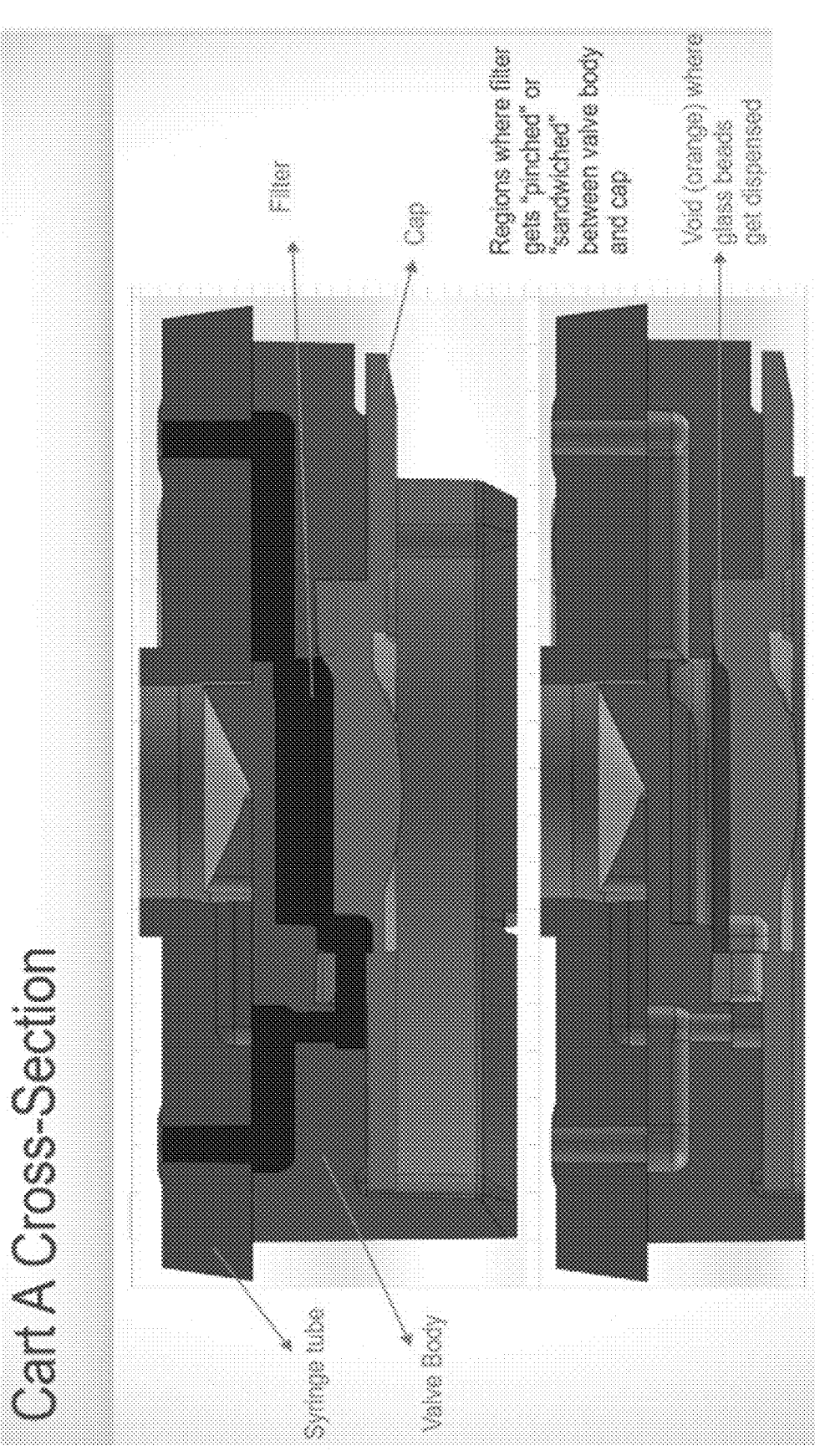
FIG. 14B illustrate cross-sectional views of a valve assembly in accordance with some embodiments.

FIG. 14A illustrate cross-sectional views of a valve assembly, in accordance with some embodiments, illustrating the gap between the filter and cap where any glass beads for mechanical lysing are filled, for comparison with the conventional valve assembly shown in FIG. 14B. In the design of FIG. 14A, the cap and valve body have been modified, as described previously, for improved fill in the void region between the filter and the cap. In FIG. 14B a thinner filter material has been used to create a larger void to facilitate glass fill. In the improved design in FIG. 14A, a thicker filter material has been used such that the void between the filter and cap is smaller, while including the posts on the gap maintain a suitable gap to facilitate the glass fill process.

Figures 14C, 14D:
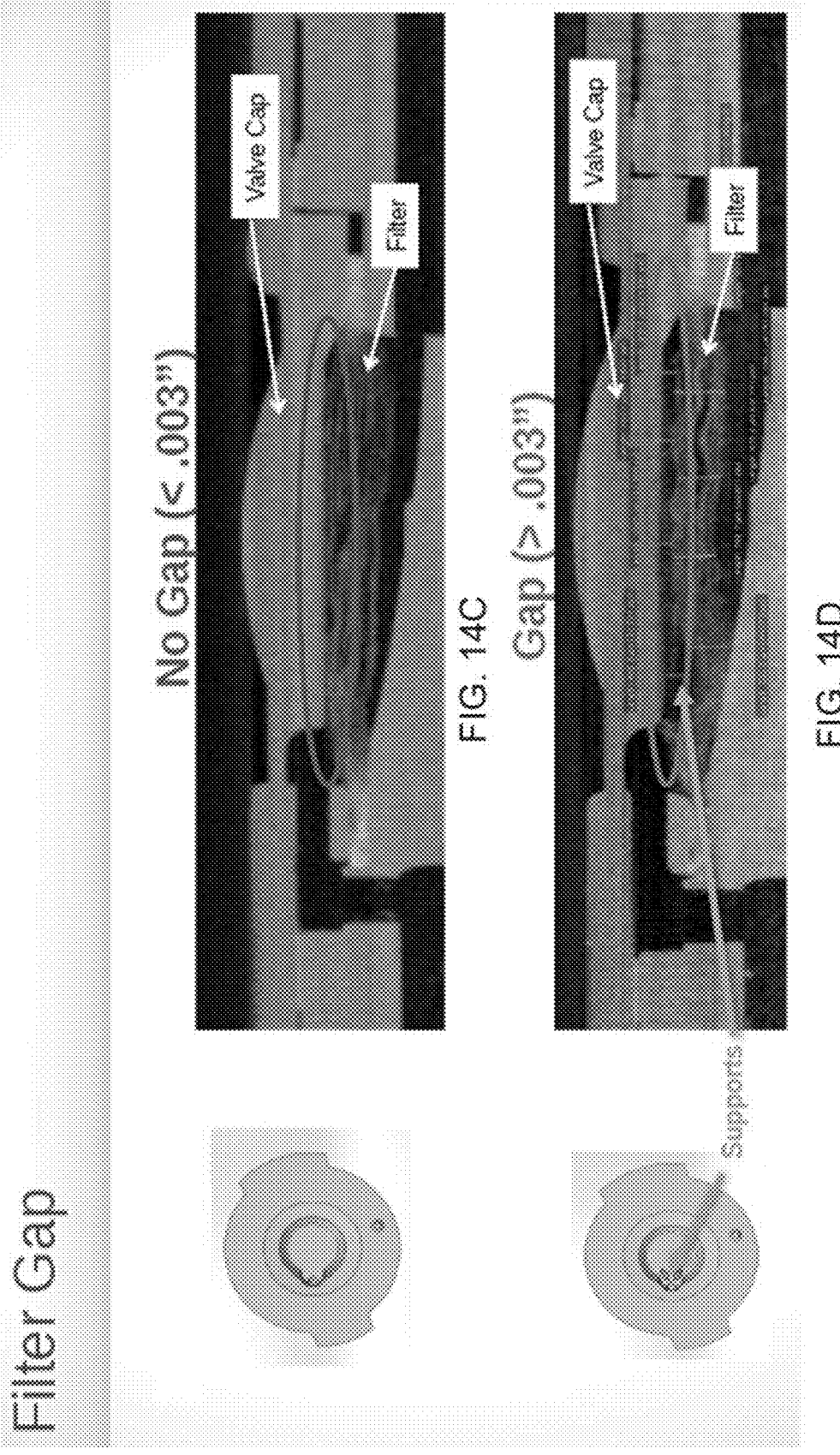
FIG. 14C illustrates a cross-sectional view of a valve assembly of a universal sample cartridge before addition of support posts.
FIG. 14D illustrates a cross-sectional view of a valve assembly of a universal sample cartridge after addition of support posts.
Figure 15B:
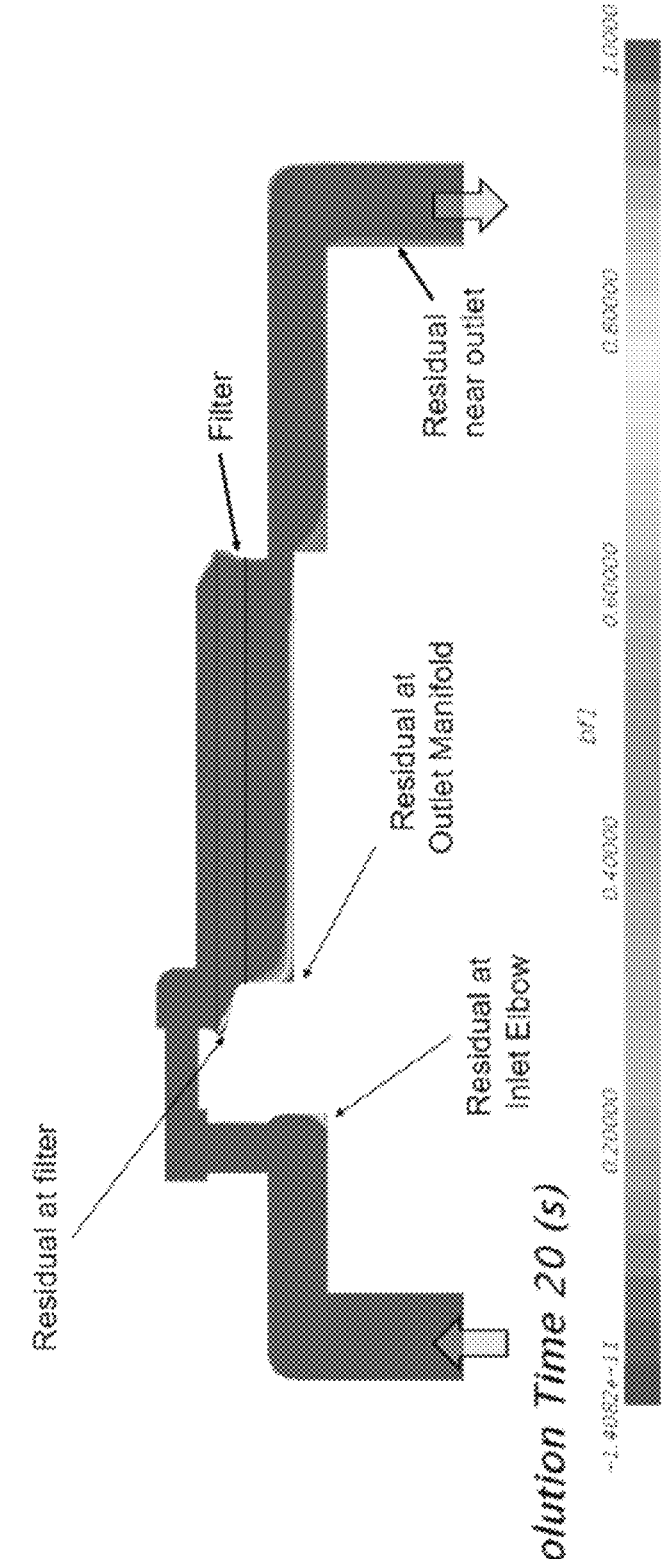
Figure 15C:
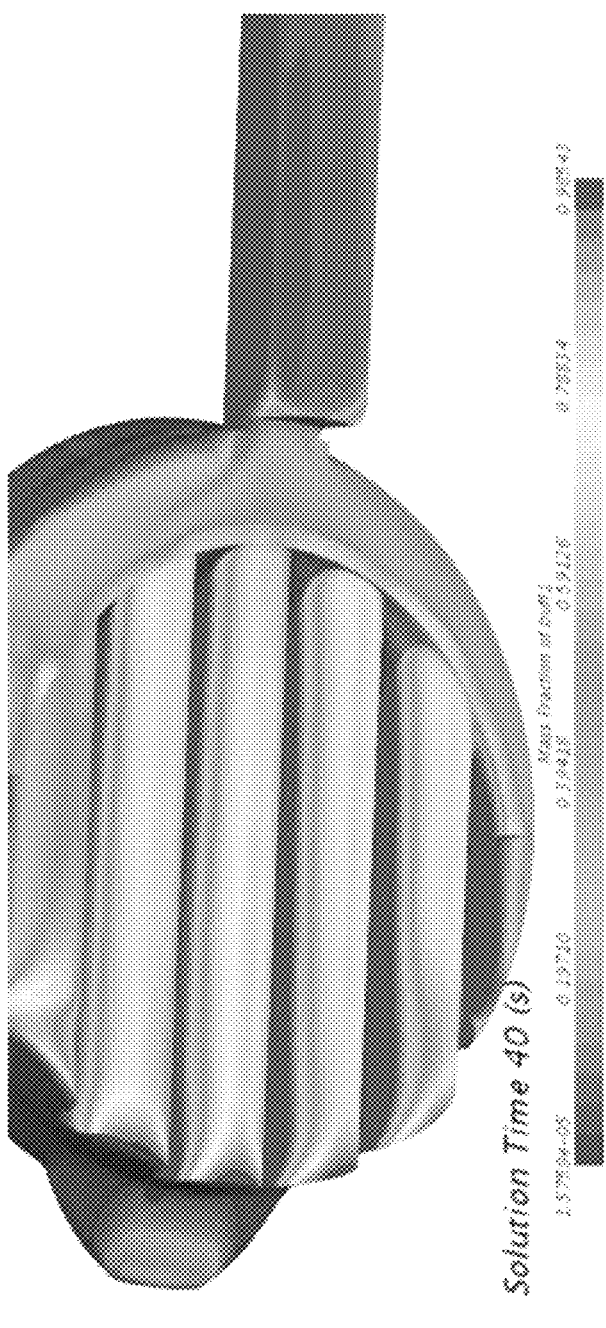
Figure 15D:
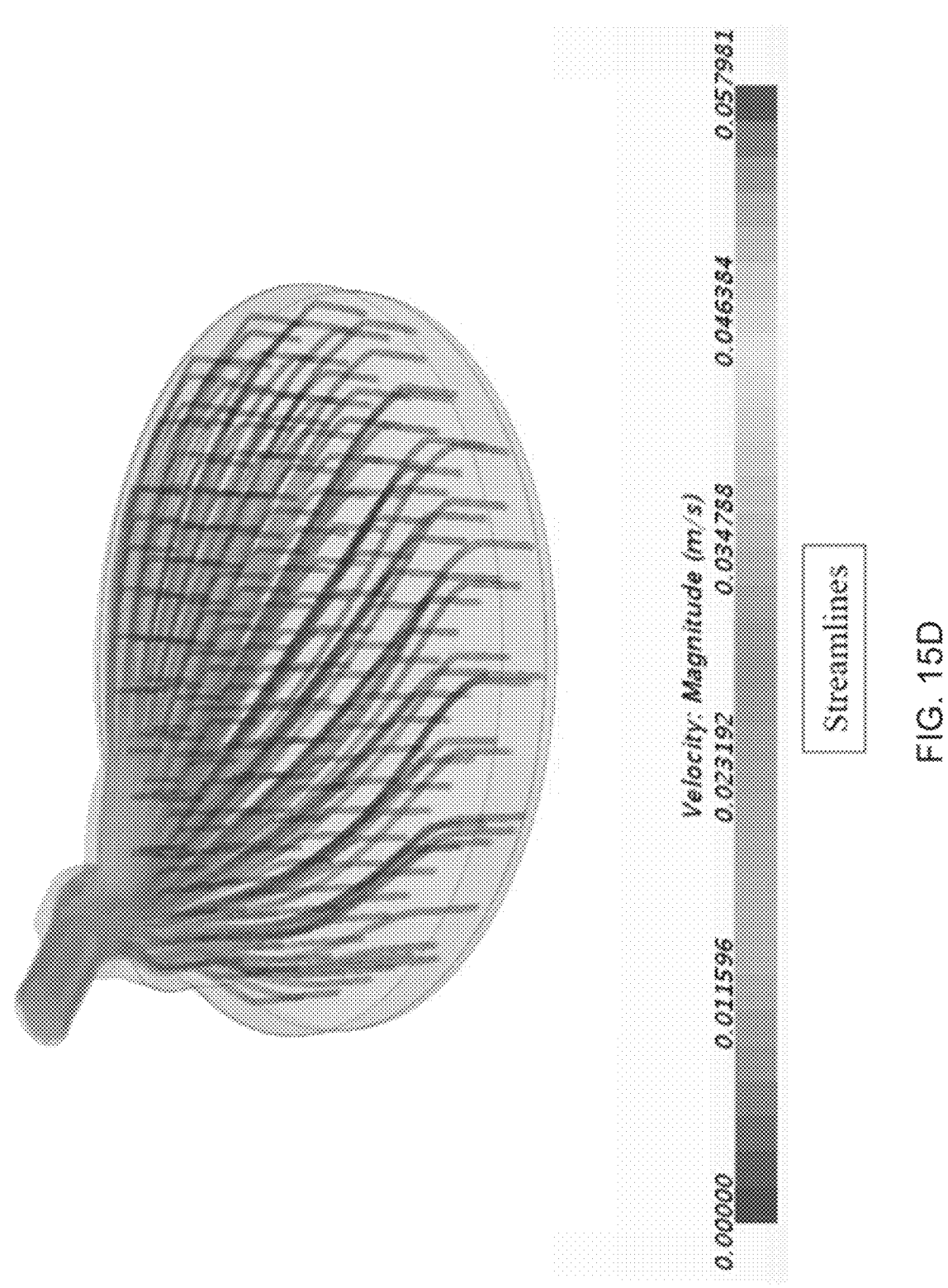
Figure 15E:
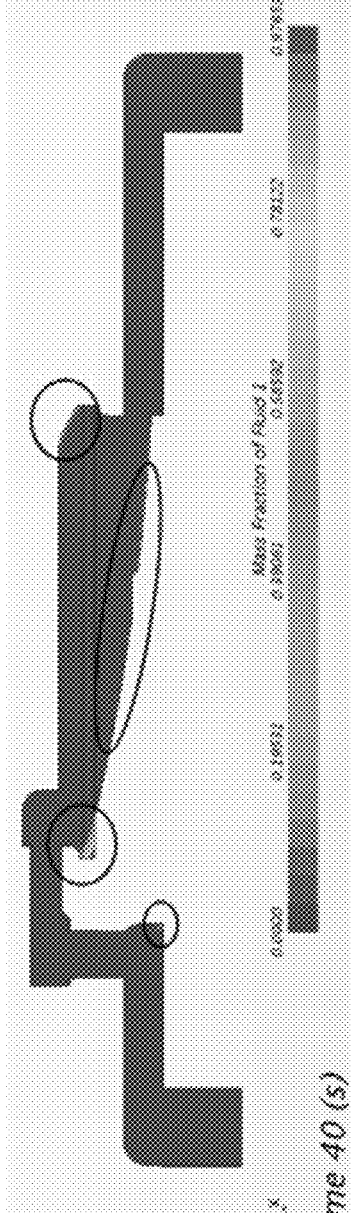
Figure 15E:
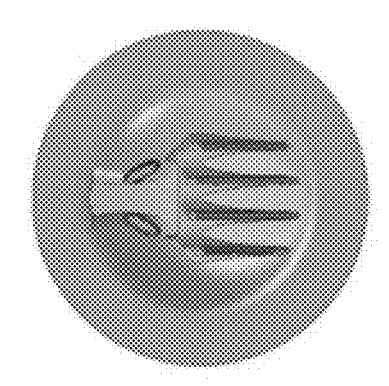
Figure 15F:
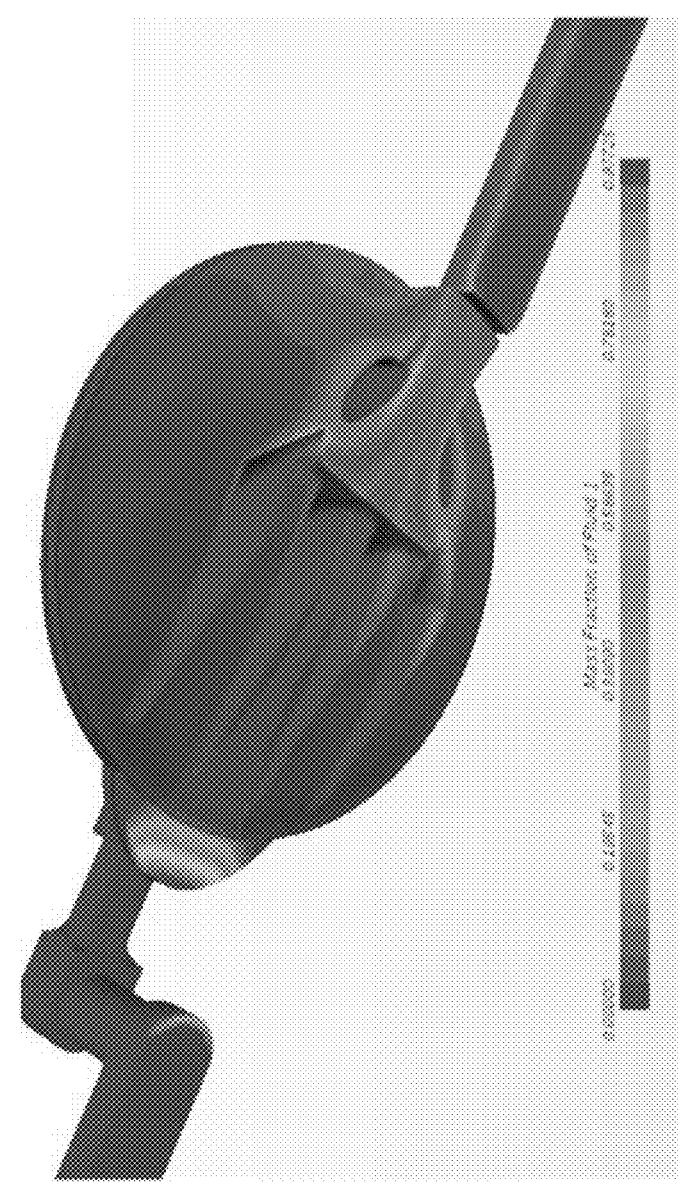
Figure 15F:
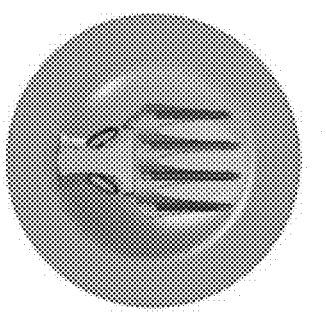
Figure 15G:
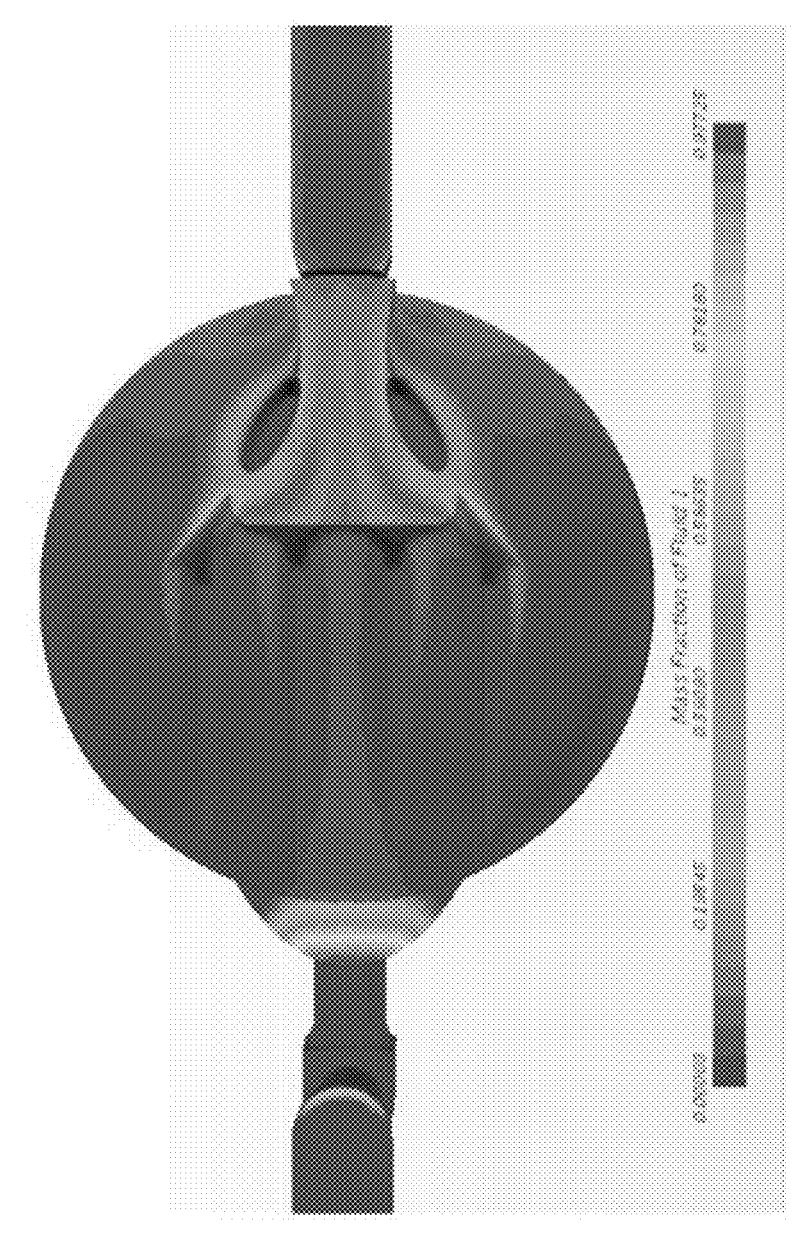
Figure 15G:
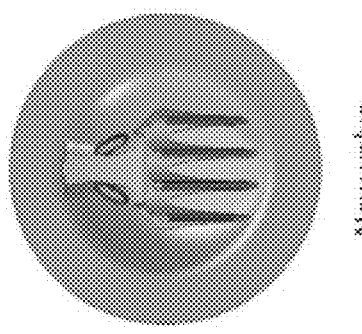
Figure 15H:
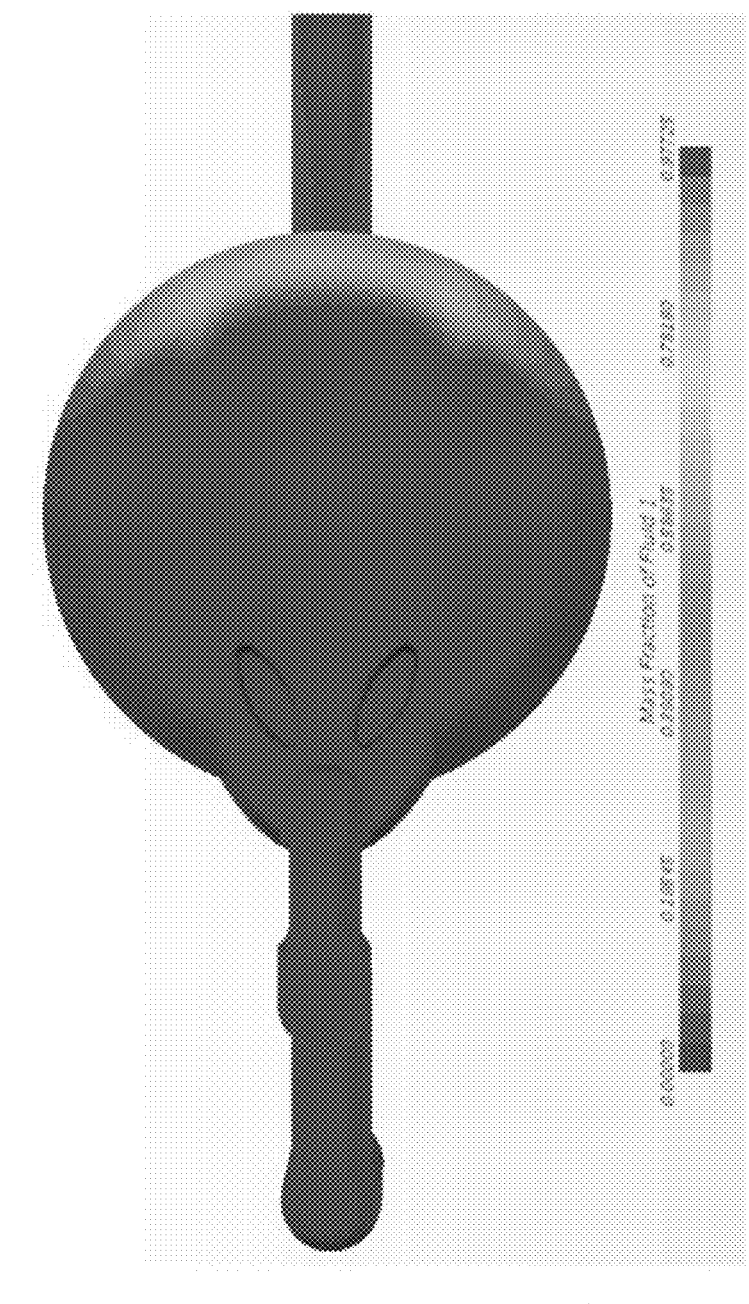
Figure 15I:
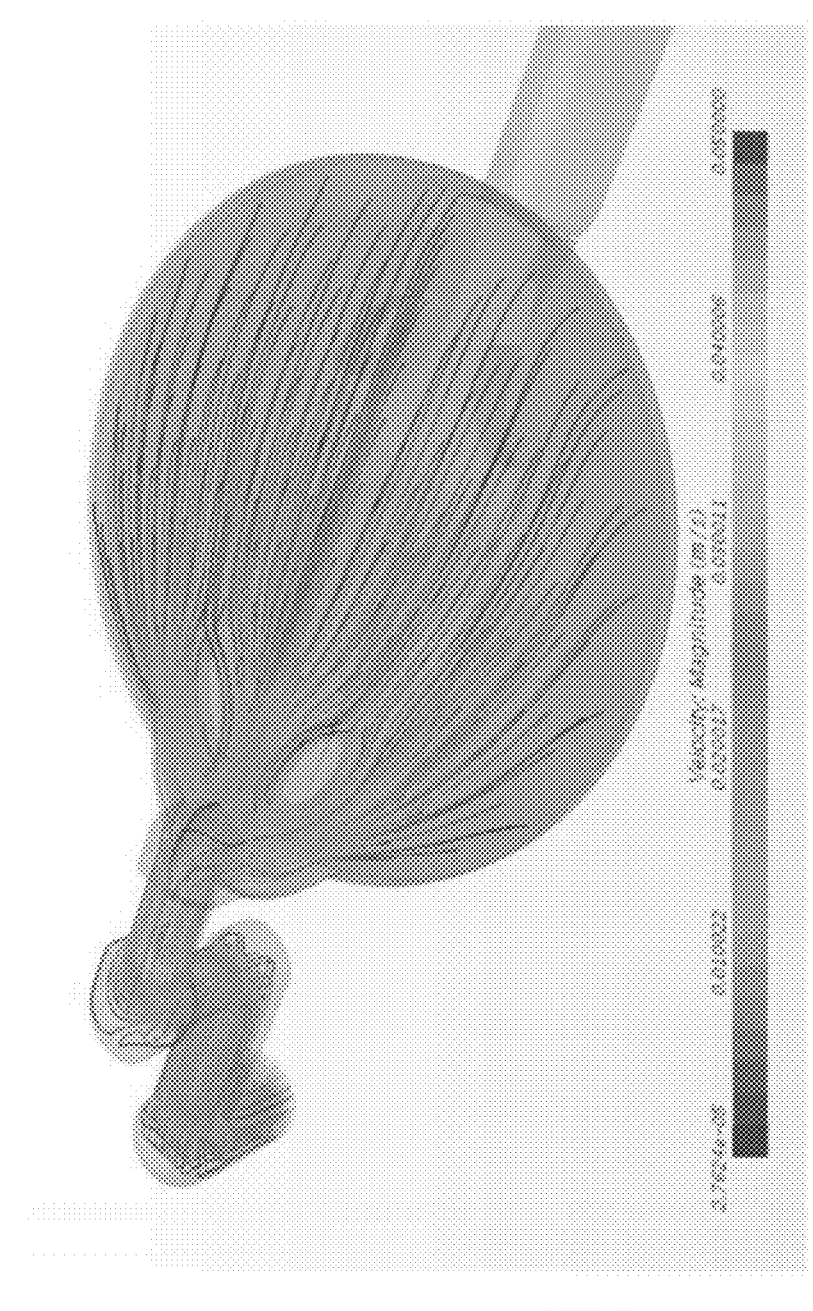
Figure 15I:
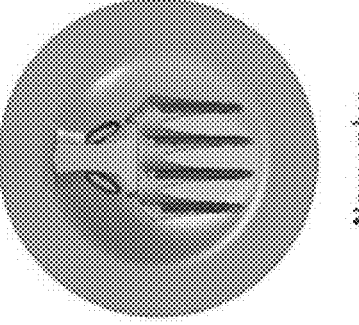
Figure 15J:
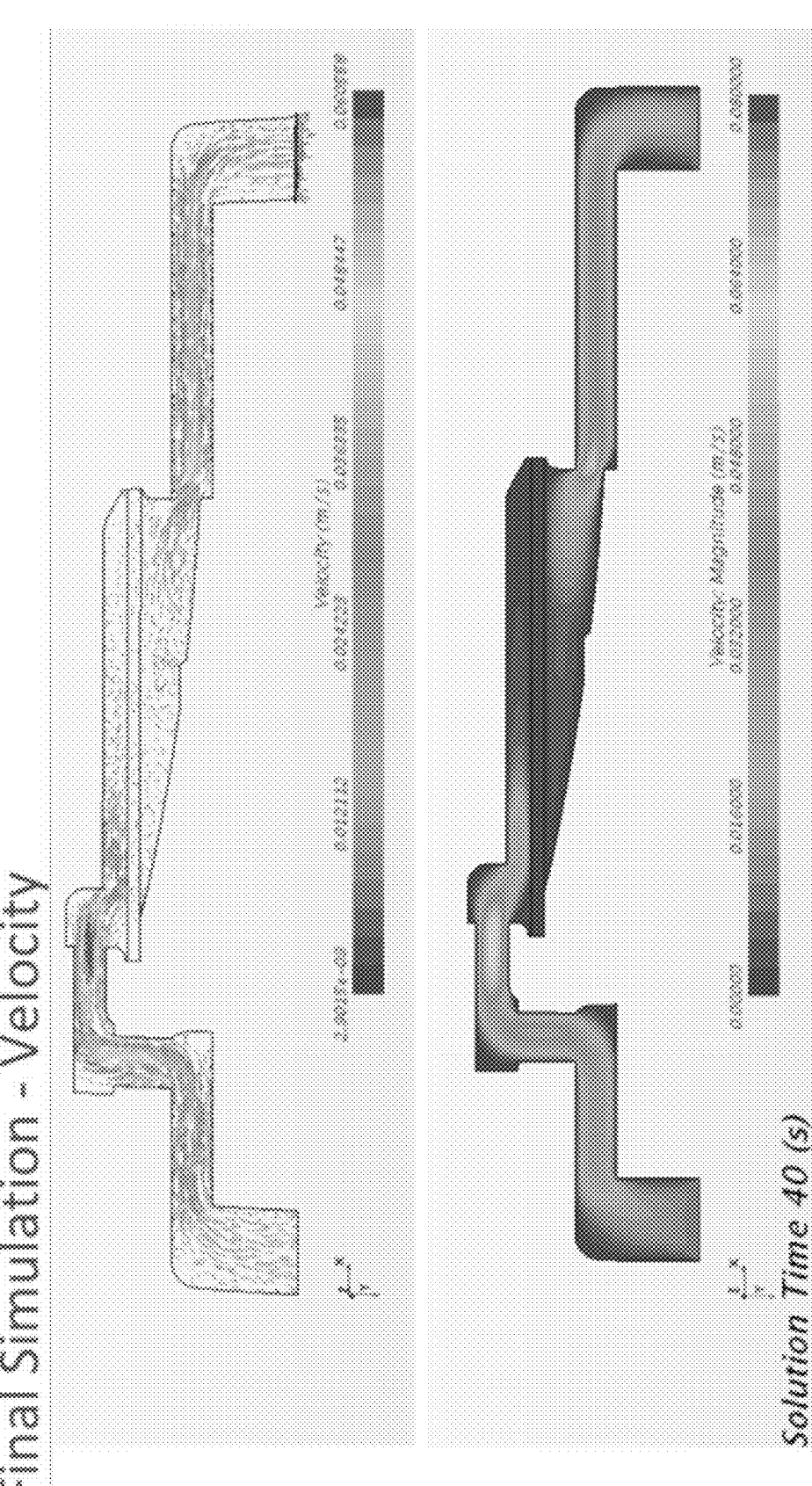
Figure 15K:
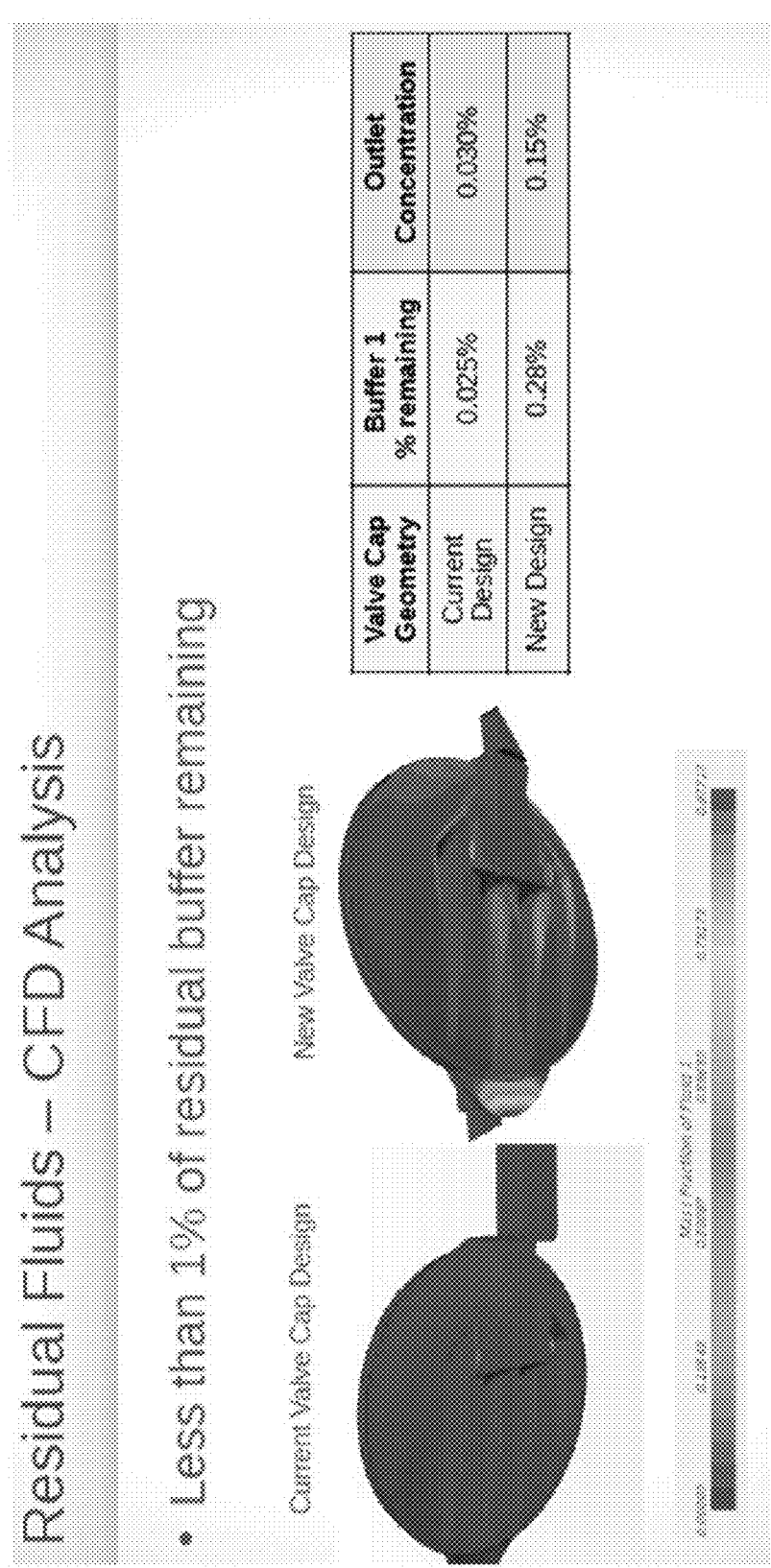

FIG. 14C illustrate cross-sectional views of a valve assembly of a sample cartridge, before addition of the posts, demonstrating an inconsistent, minimal gap between the filter and the valve cap under some conditions. FIG. 14D shows the valve assembly with the addition of posts, which provides a more consistent, enlarged gap to facilitate glass infill.

III. Experimental Results as to Performance Characteristics

FIG. 15A-15K illustrate various models of a valve assembly for a universal sample cartridge, in accordance with some embodiments. In particular, the models demonstrate the improved washing of residual buffer through the flow-path of the valve assembly, see FIGS. 15B-15K. In some embodiments, improved washflow of buffer and reduction of buffer carryover is achieved by streamlining the fluid flow path through the inlet and outlet of the valve assembly. In this embodiment, the fluid flow path is streamlined by smoothing any transitions and eliminating any sharp (e.g. 90 degree) corners.

Figure 16:
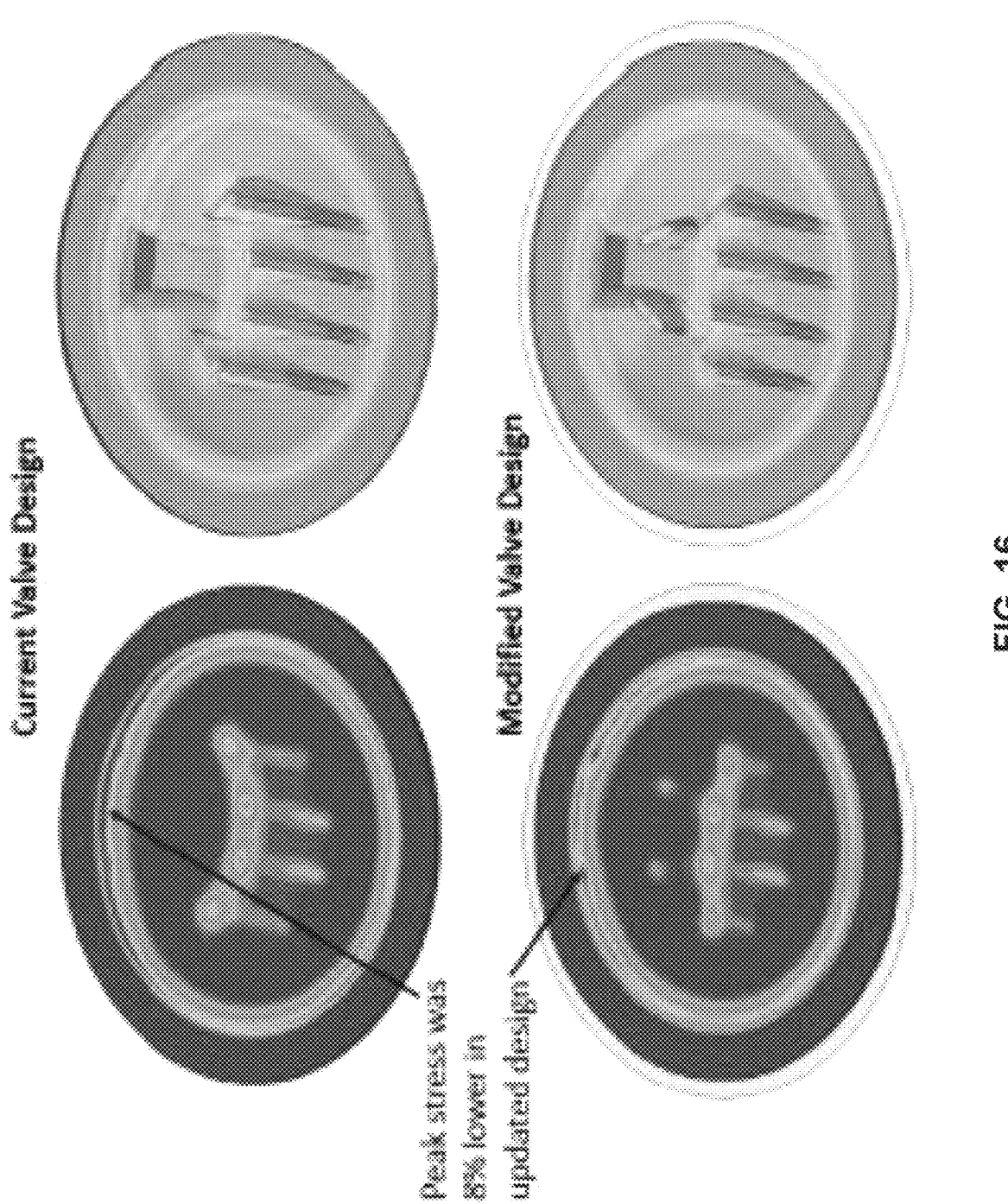
FIG. 16 illustrates stress distribution of a valve assembly of a universal sample cartridge, in accordance with some embodiments, as compared to a conventional valve design.

FIG. 16 demonstrates the marked advantages of the improved valve design support protrusions over conventional designs in regard to filter stress. As shown by the finite element analysis in FIG. 16, the peak stress in the valve body with the pair of support posts adjacent the outlet was 8% lower than in the conventional design without any support posts.

Figure 17:
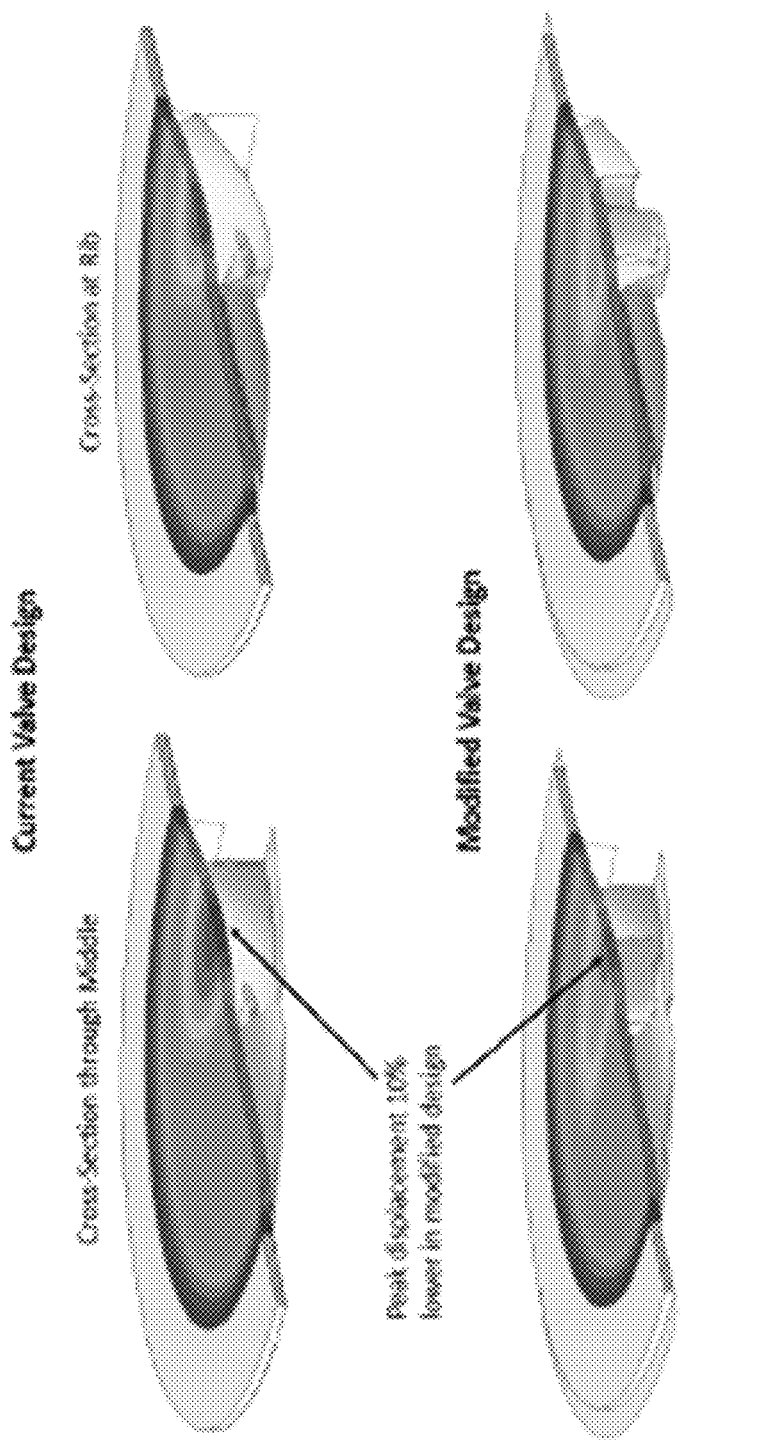
FIG. 17 illustrates filter displacement of a valve assembly of a universal sample cartridge, in accordance with some embodiments, as compared to a conventional valve design.

FIG. 17 demonstrates the marked advantages of the improved valve design having support protrusions over conventional designs in regard to vertical displacement of the filter. As shown by the finite element analysis in FIG. 16, the peak displacement in the filter supported by the pair of support posts adjacent the outlet was 10% lower than in the conventional design without any support posts.

Figure 18:
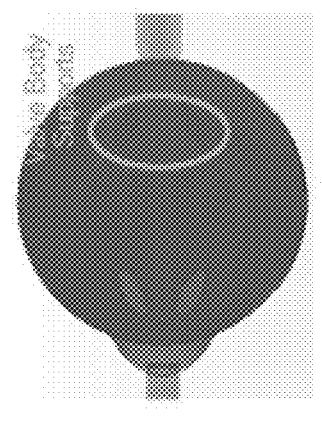
FIG. 18 illustrates washout of residual buffer of a valve assembly of a universal sample cartridge, in accordance with some embodiments, as compared to a conventional valve design.
Figure 18:
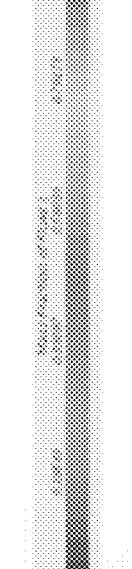

FIG. 18 demonstrates that the use of support posts in the improved valve design did not significantly impact wash out of residual buffer. As can be seen in computation fluid dynamics analysis of FIG. 18, there was 0.28% buffer remaining and an outlet concentration of 0.15% in the conventional design, and in the improved valve body design, there was 0.38% and 0.28% outlet concentration. These results demonstrated comparable wash out and residual buffer between the two designs.

Figure 19:
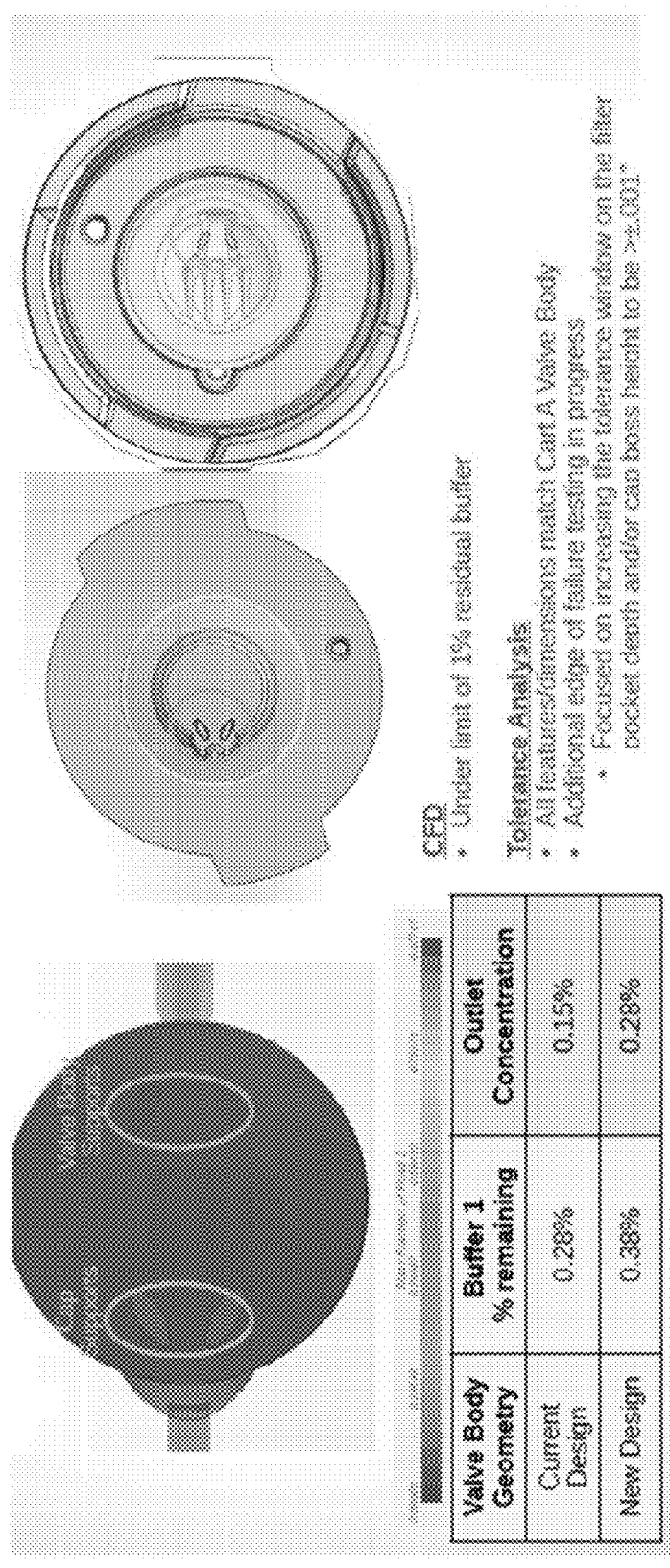
FIG. 19 illustrates buffer carryover of a valve assembly of a universal sample cartridge, in accordance with some embodiments, as compared to a conventional valve design.

FIG. 19 illustrates experimental results as to buffer carryover of a valve assembly of a multi-assay sample cartridge, in accordance with some embodiments, as compared to a conventional valve designs. As shown, the results demonstrates that the addition of the posts did not significantly impact buffer carryover.

Figure 20A:
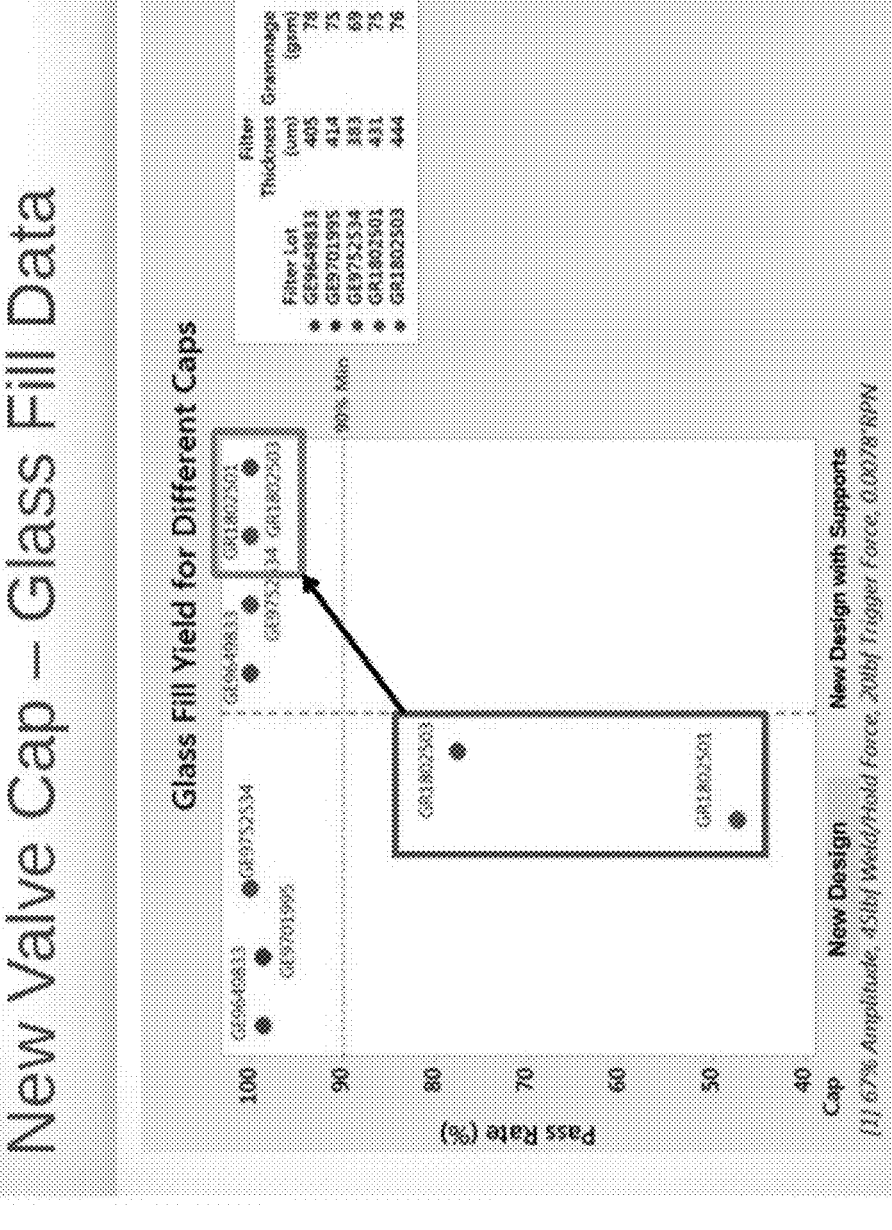
FIGS. 20A-20G show experimental results showing fill and performance data of a valve assembly of universal assay sample cartridge, in accordance with some embodiments, before and after addition of support posts.
Figure 20B:
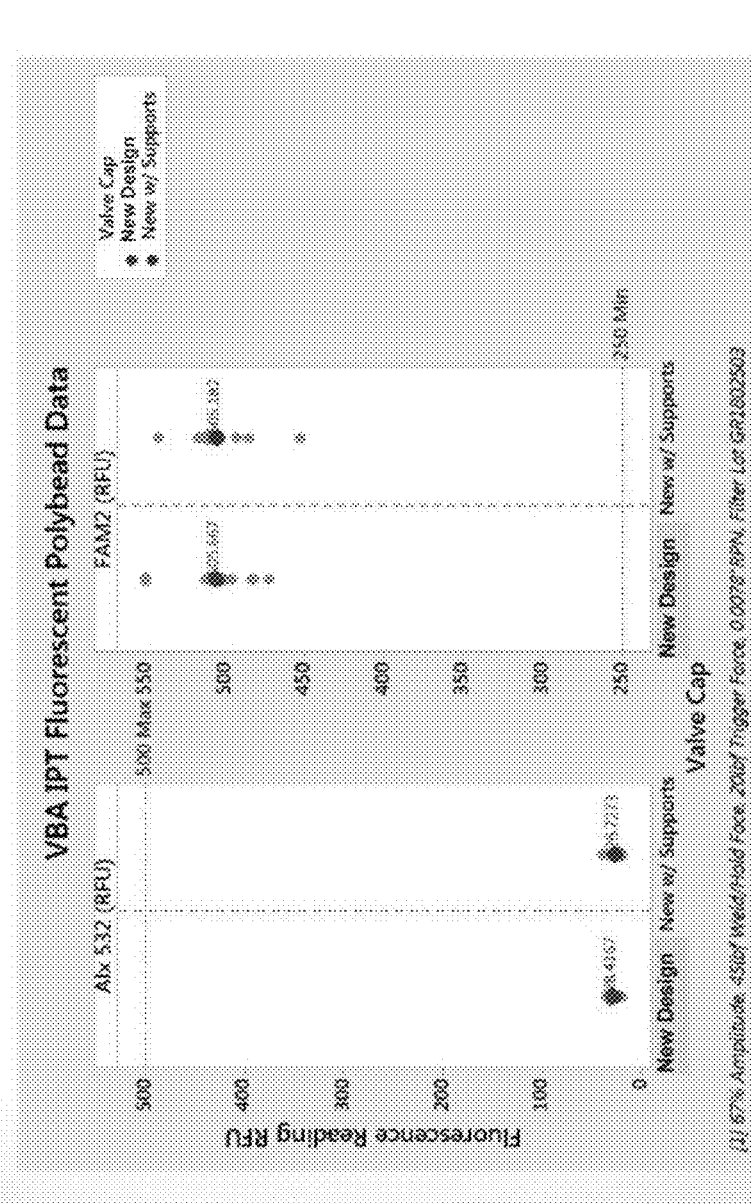
Figure 20C:
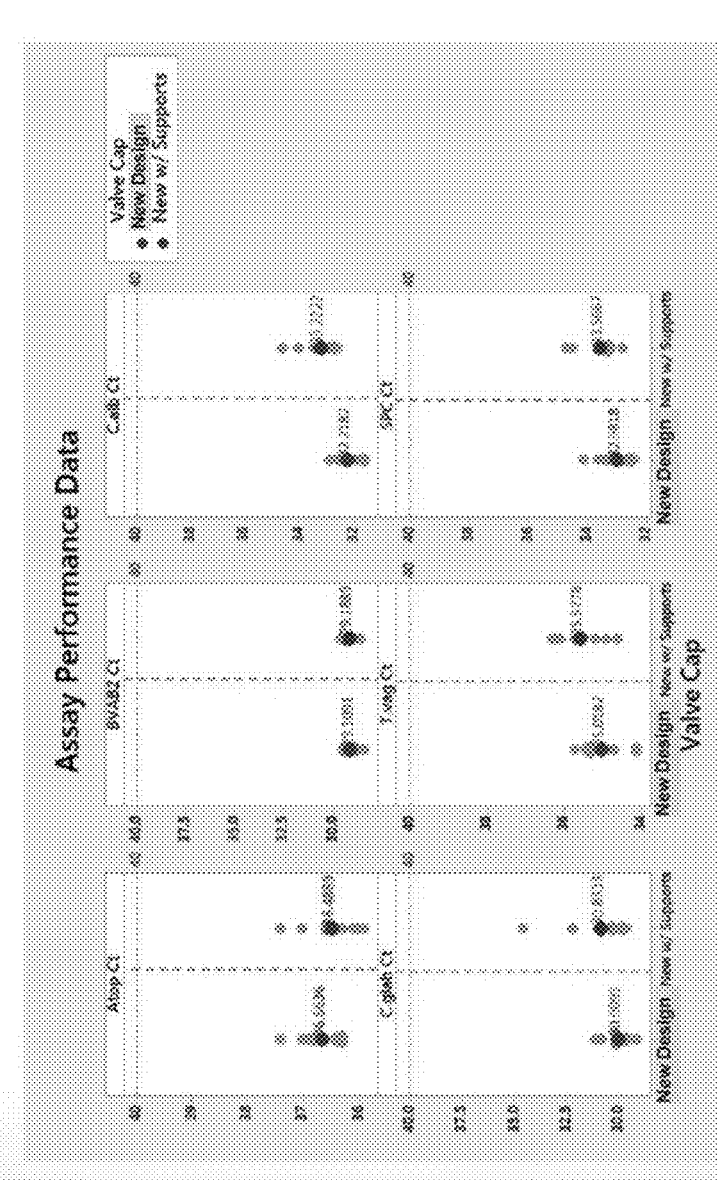
Figure 20D:
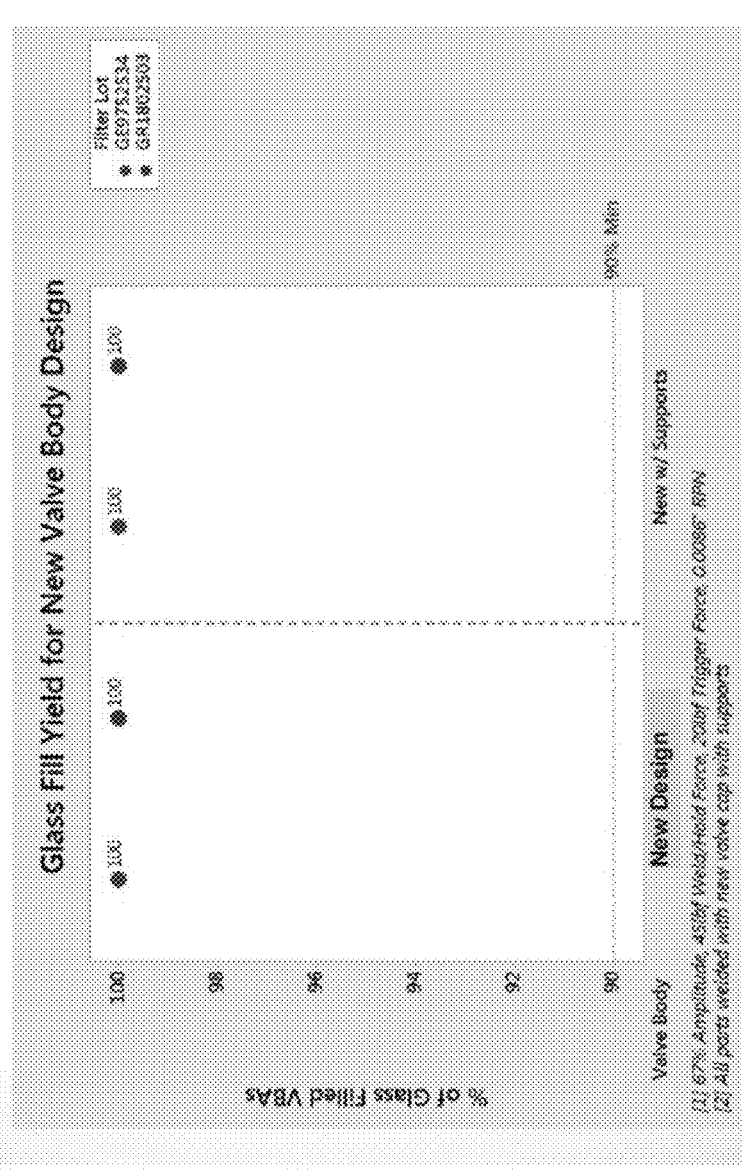
Figure 20E:
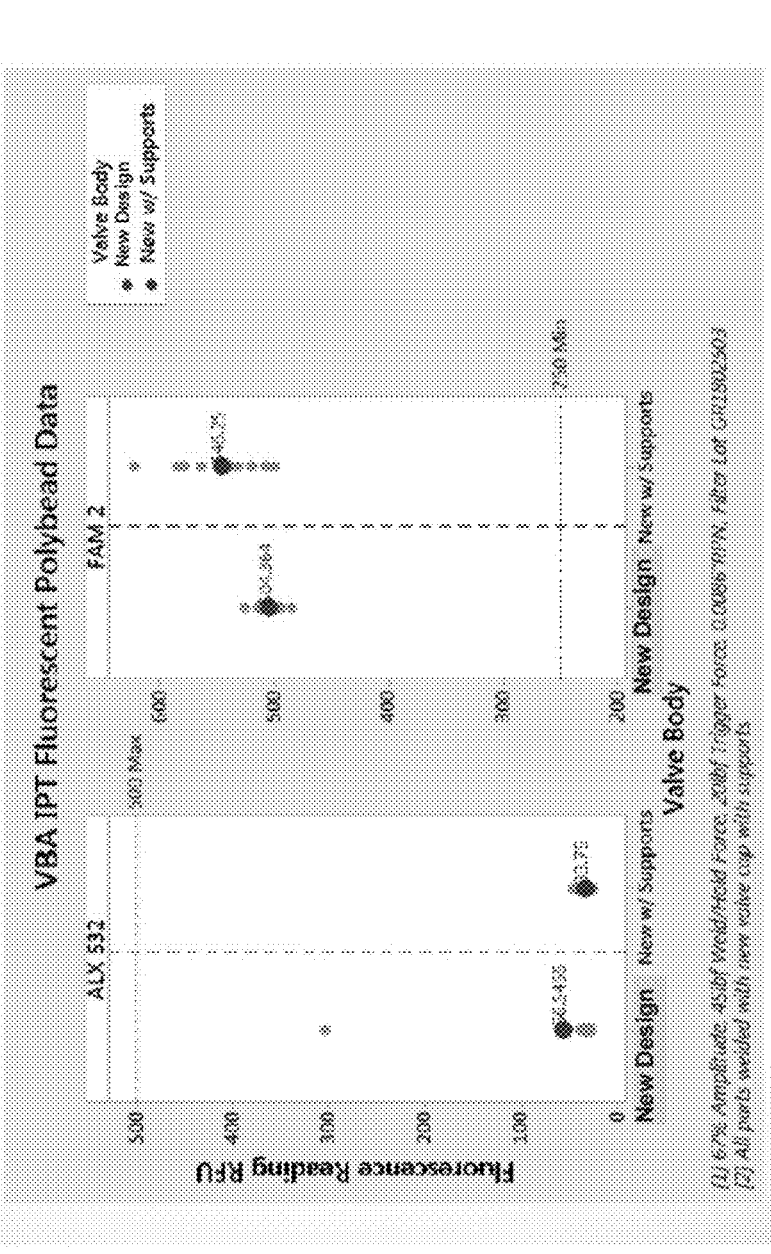
Figure 20F:
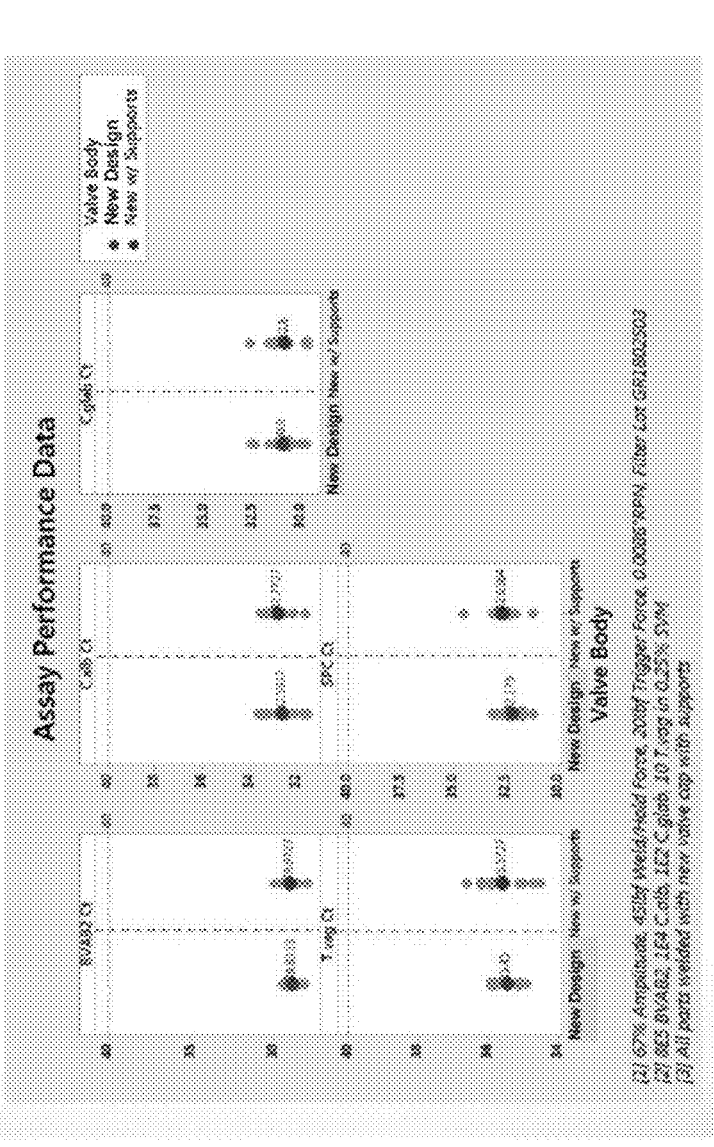
Figure 20G:
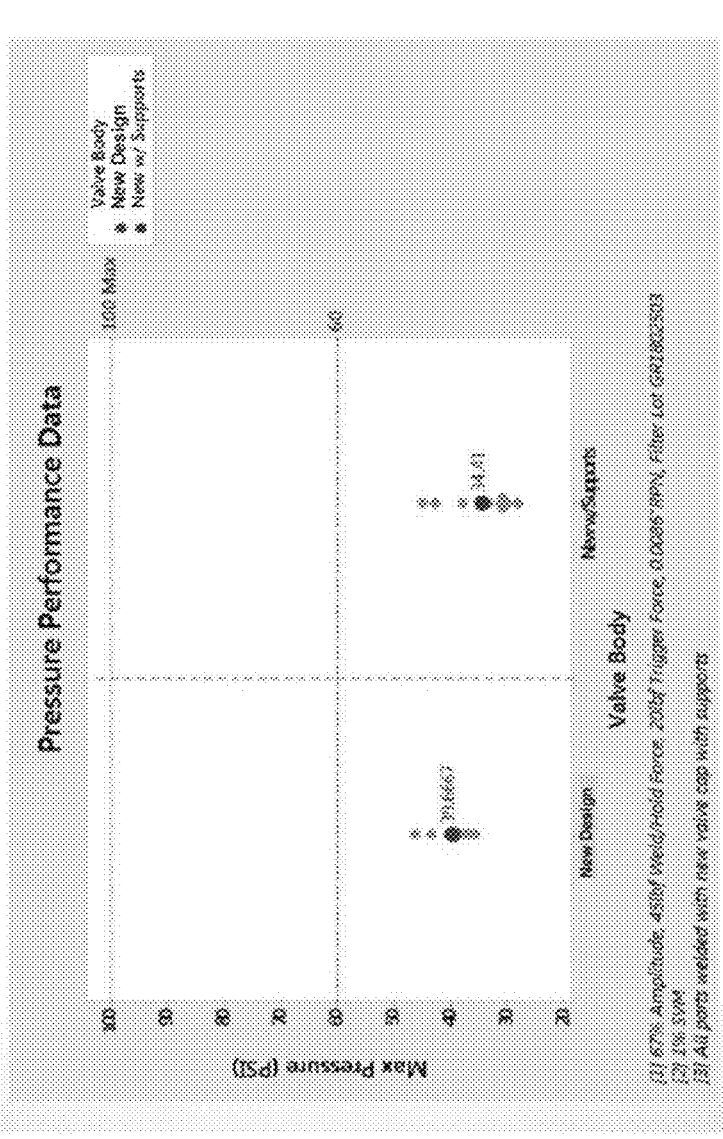

FIGS. 20A-20G show experimental results illustrating fill and performance data of a valve assembly of universal assay sample cartridge, in accordance with some embodiments, before and after introduction of support posts. FIG. 20A shows glass fill ability improves to over 90% with the valve design with the support post features that maintain the filter placement to cap gap thereby improving fill. FIG. 20B shows filter integrity and capture ability are not affected by the added support features. FIG. 20C shows similar functional performance between the two cap designs. FIG. 20D shows the glass fill ability is not negatively impacted by the addition of the posts. FIG. 20E shows that the filter integrity and capture ability are not affected by the added support features. FIG. 20F shows similar functional performance between the two valve body designs. FIG. 20G shows that maximum pressures were reduced by 5 psi with the added support features of the new design.

IV. Assay WorkFlows

In one aspect, the sample cartridge having an improved valve assembly, as described herein, is capable of a variety of workflows that perform: chemical lysing of targets, mechanical lysing of targets, or both. Accordingly, the sample cartridge can perform an existing workflow associated with conventional specialized cartridges, or can perform entirely new workflows that perform both.

Figure 21:
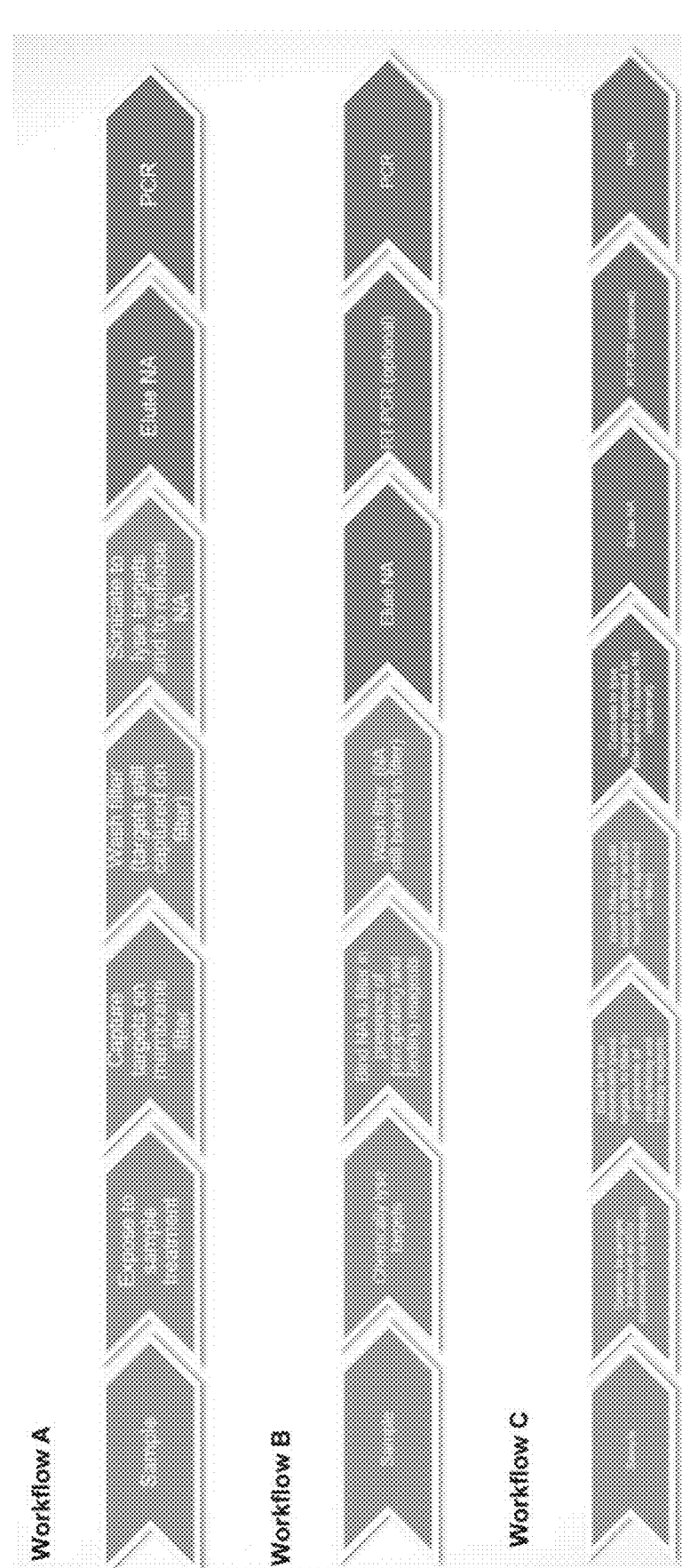
FIG. 21 depicts various assay workflows, in accordance with some embodiments.
Figure 22A:
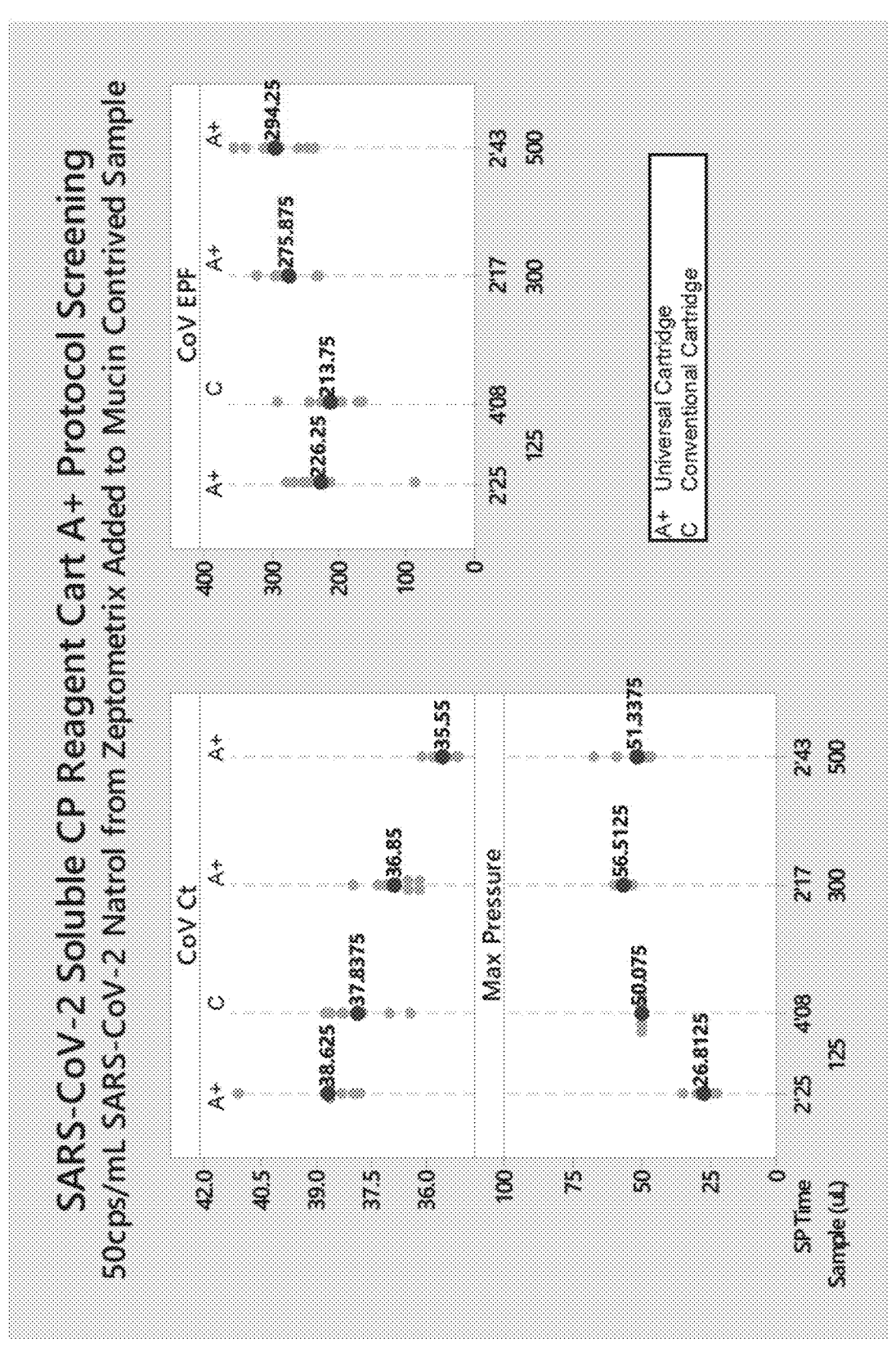
FIGS. 22A-22D show experimental results illustrating substantially reduced sample processing times allowed by the universal cartridge design, in accordance with some embodiments.
Figure 22B:
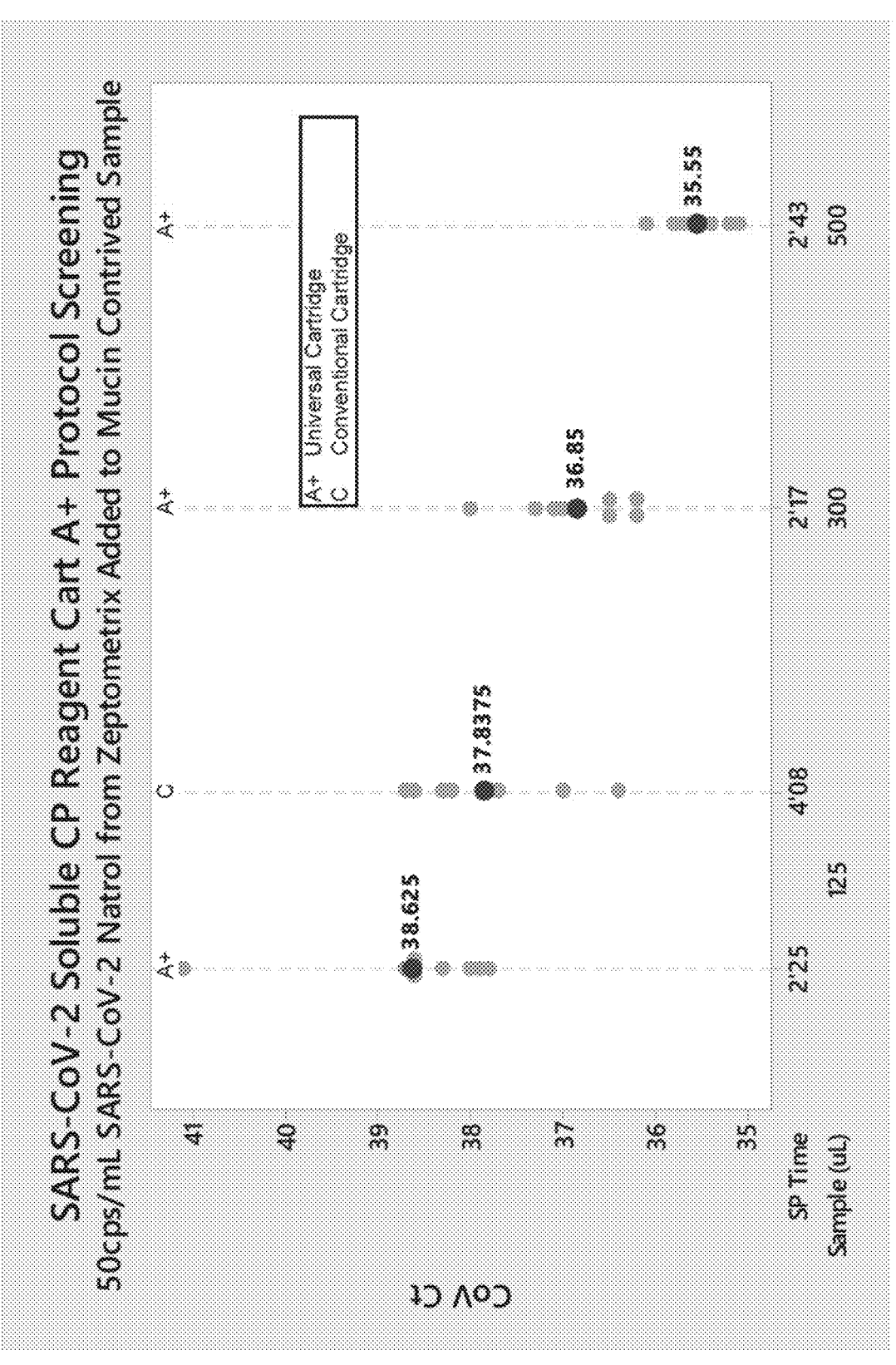
Figure 22C:
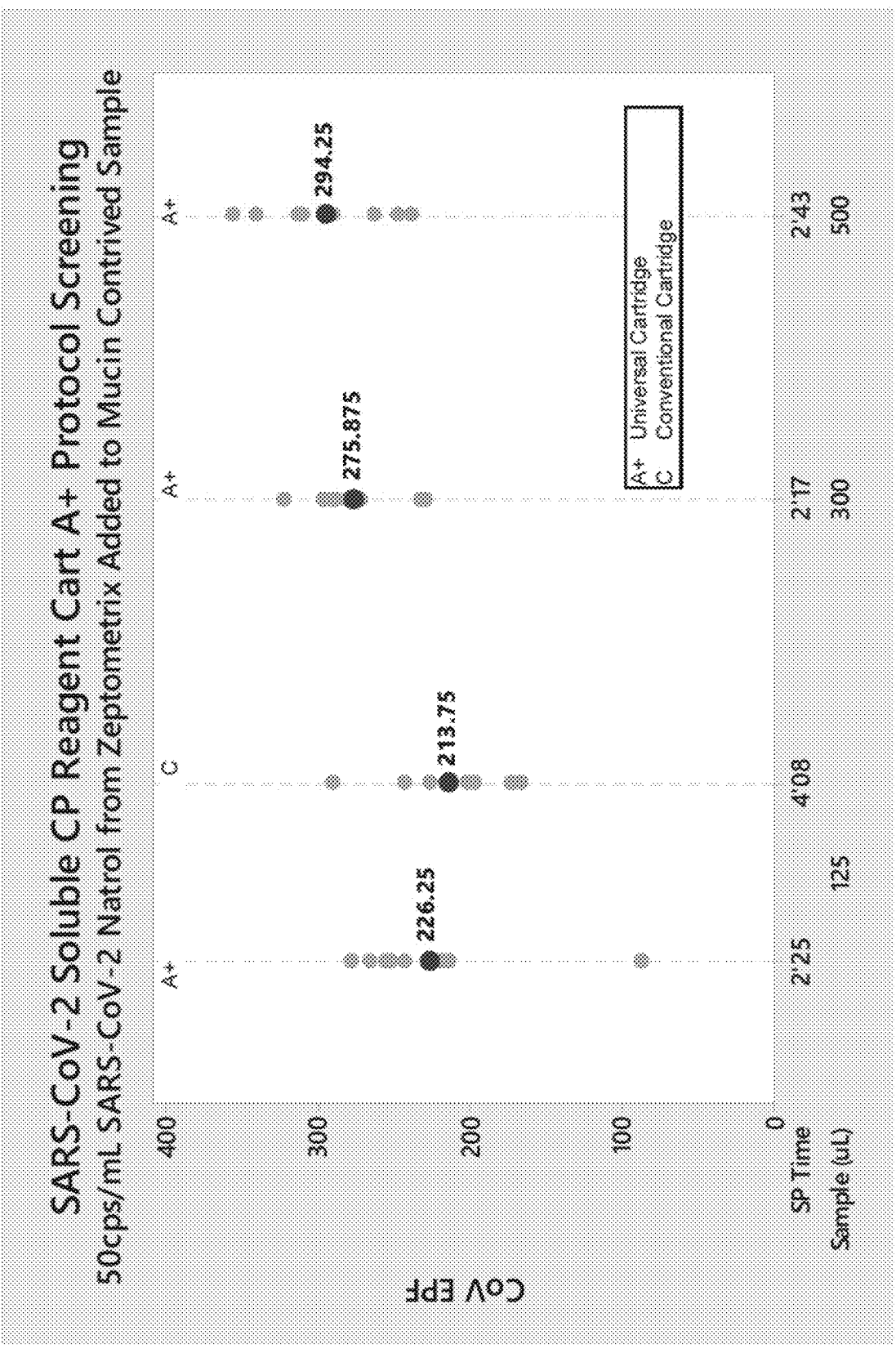
Figure 22D:
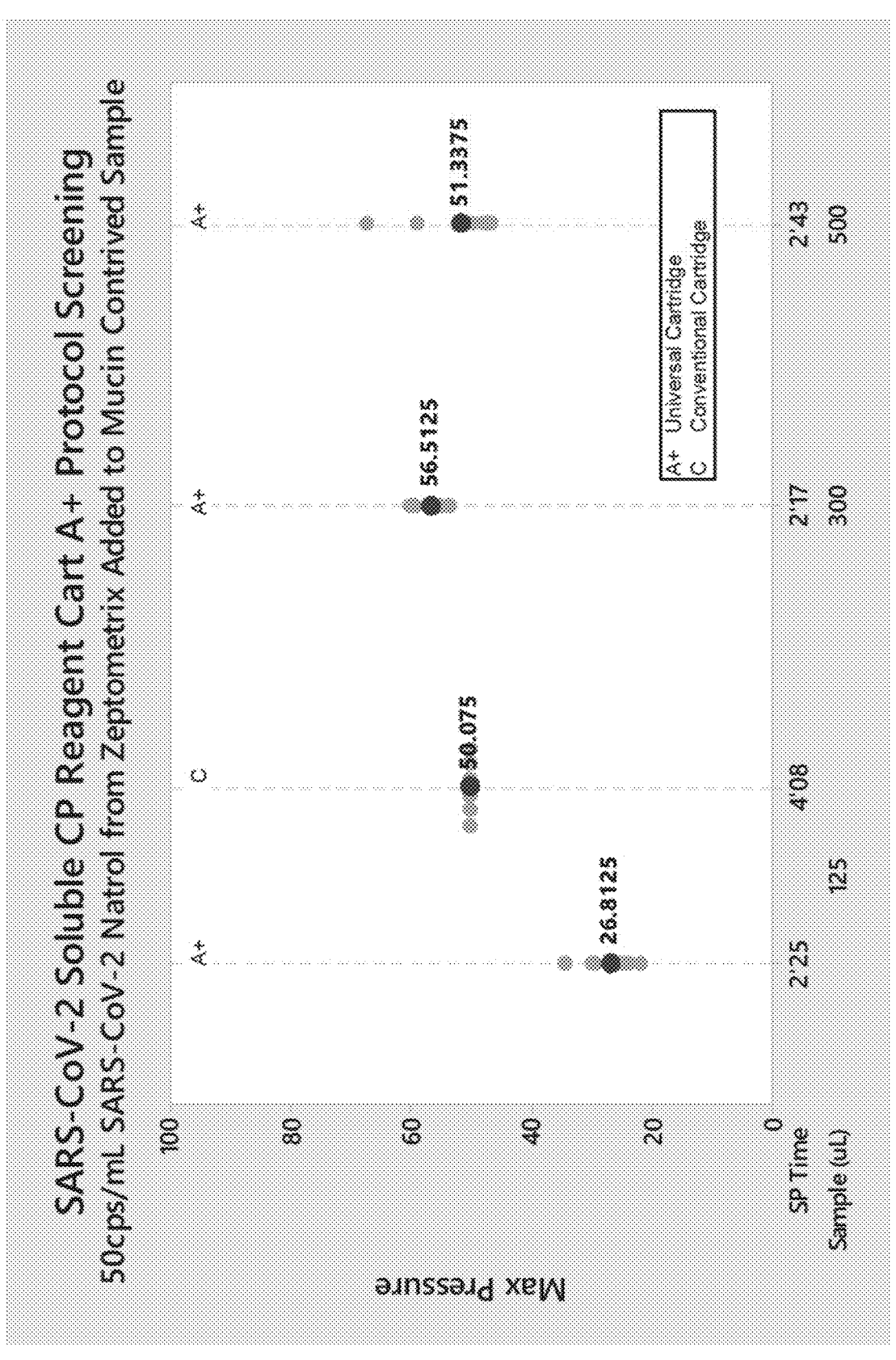
Figure 23A:
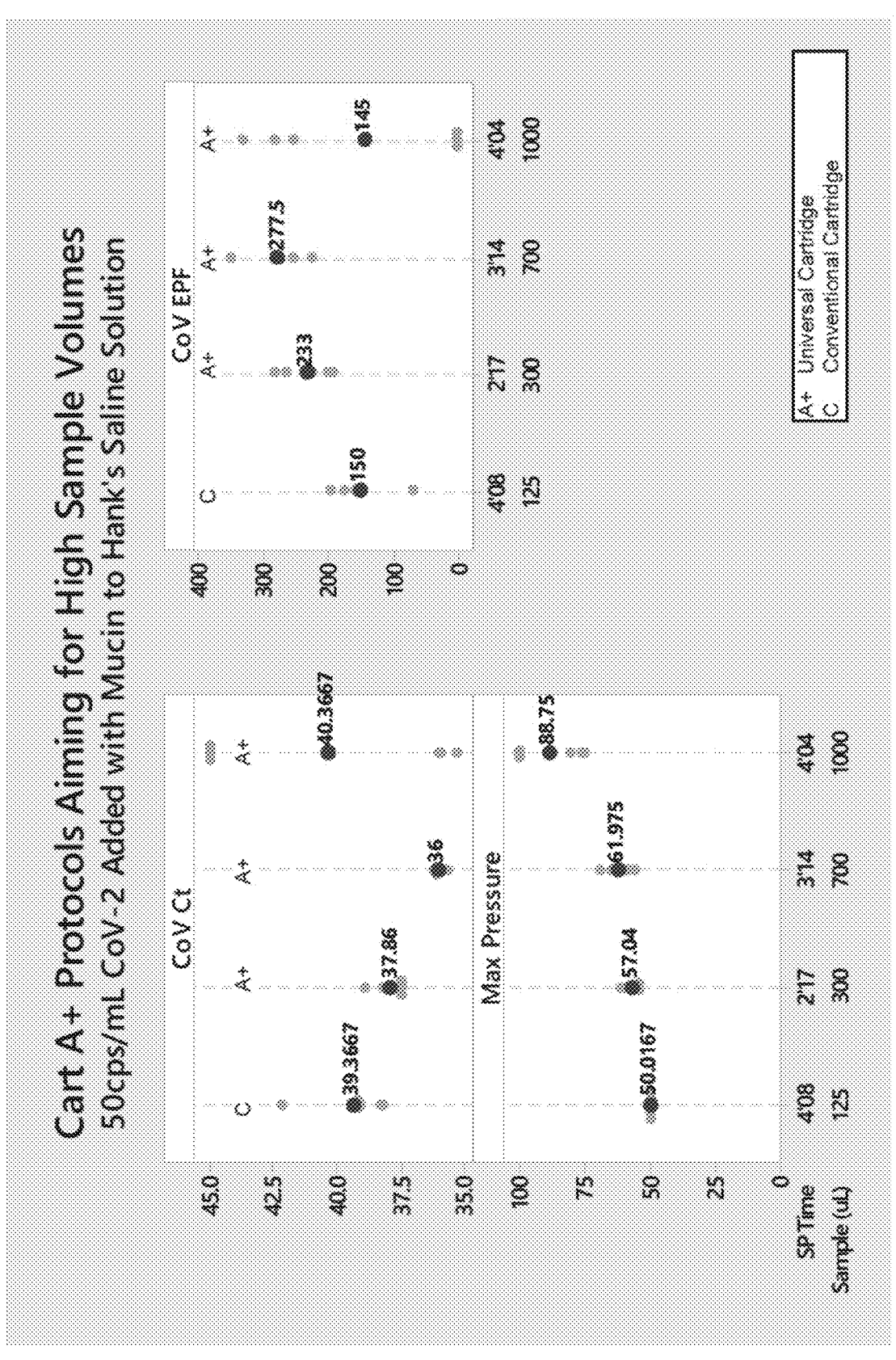
FIGS. 23A-23D show experimental results illustrating higher sampling volumes allowed by the universal cartridge design, in accordance with some embodiments.
Figure 23B:
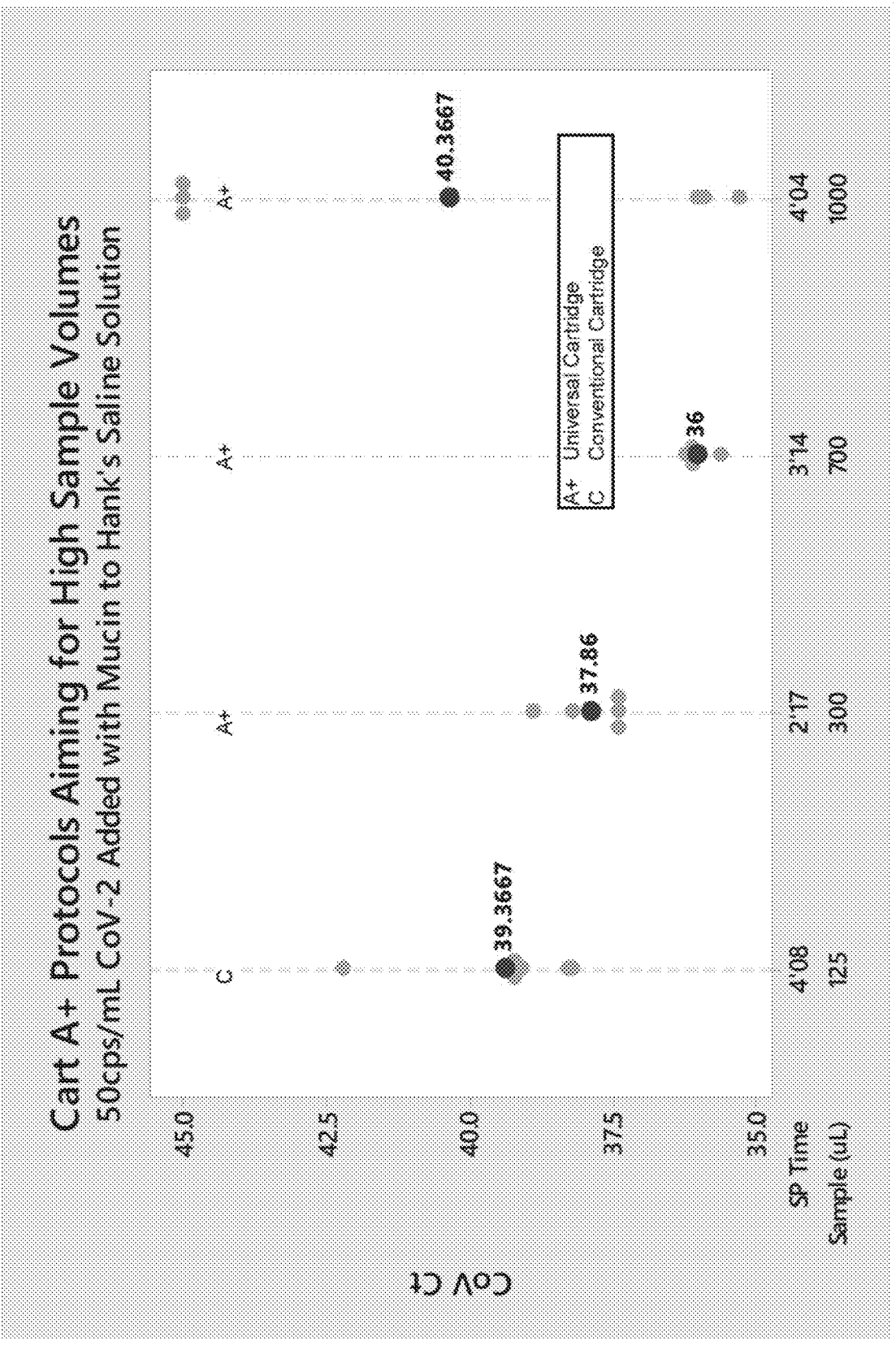
Figure 23C:
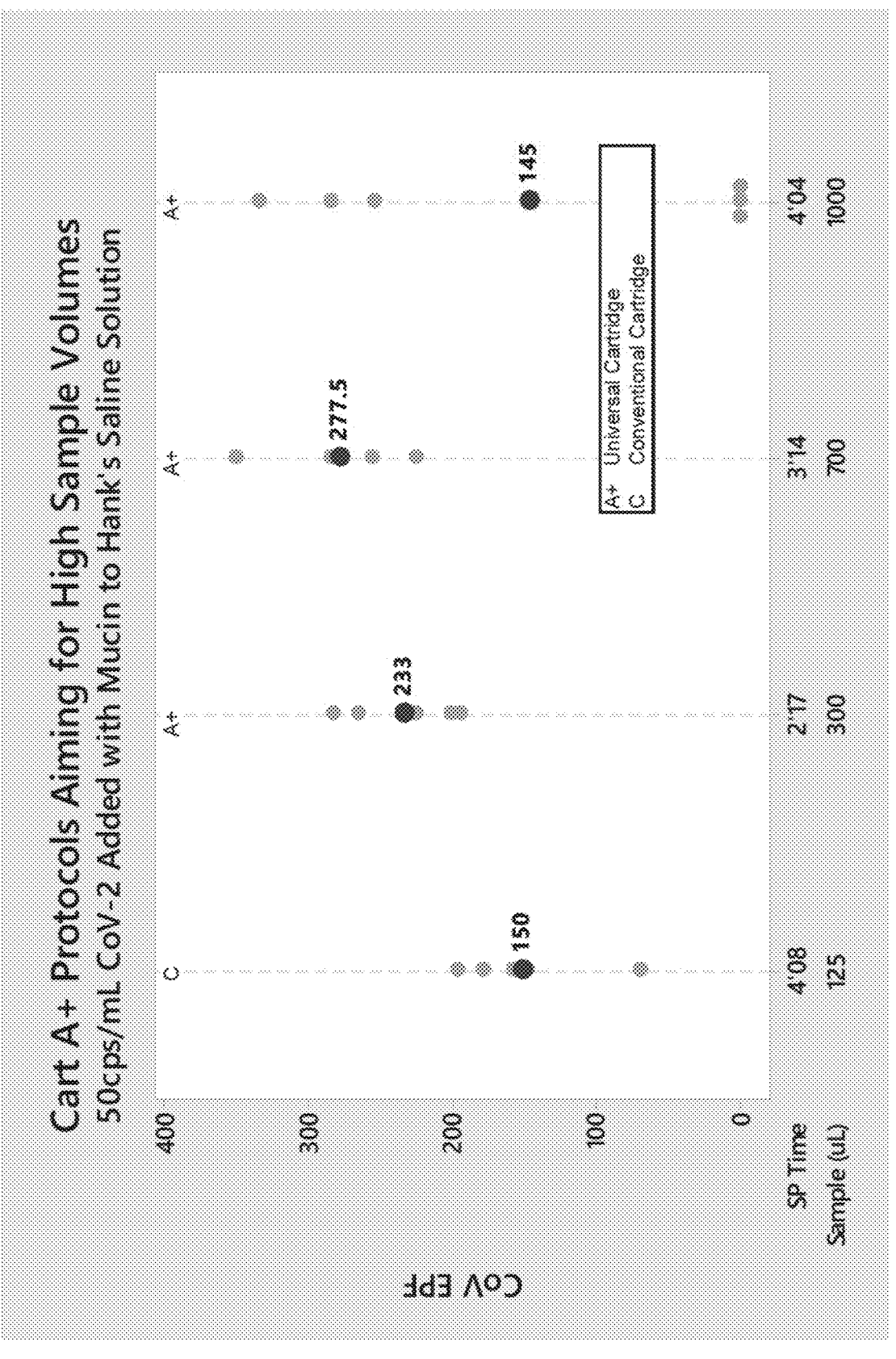
Figure 23D:
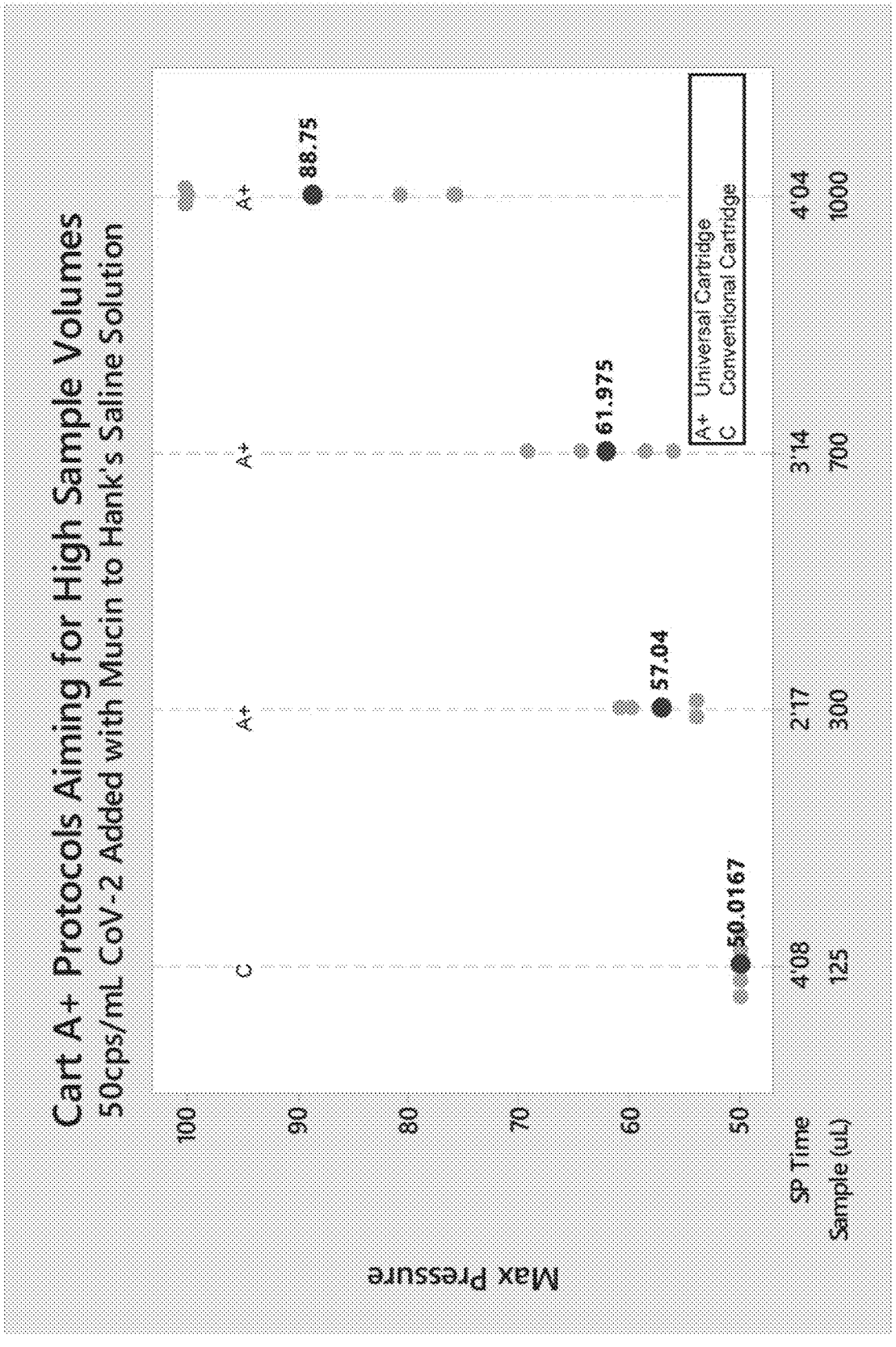

Exemplary assay workflows that can be performed with a single universal cartridge, in accordance with some embodiments, is shown in FIG. 21. In any of these embodiments, the filter can be formed of glass filter to promote affiniting binding of the nucleic acids (NA) to the glass fibers and a pore size suited for chemical lysing as well. In any of these workflows, the nucleic acid amplification can be PCR, real-time PCR, isothermal amplification (including but not limited to nucleic acid sequence-based amplification, loop-mediated isothermal amplification, helicase-dependent amplification, rolling circle amplification, multiple displacement amplification, whole genome amplification or recombinase polymerase amplification) or other nucleic acid amplification methods known to persons of skill in the art.

In Workflow A, the sample is optionally exposed to a sample treatment or chemically lysed, then the treated or lysed fluid sample is flowed through the filter where targets are captured. In some embodiments, the sample treatment is used to either weaken the cell wall or to inactivate the sample or make it less viscous to facilitate being processed through the filter. The filter is then washed, leaving the targets on the filter. Next, the targets are mechanically lysed, such as by sonication, to release nucleic acid (NA). In some embodiments, mechanical lysing includes in-filling glass beads along the filter to aid in mechanical lysing of the target. Next, the NA is eluted from the filter and then nucleic acid amplification is performed is performed.

In Workflow B, the sample is chemically lysed to obtain the NA targets. In some embodiments, after chemically lysing, the NA is bound to the filter by the presence of precipitating and binding reagent. Next, the filter is washed with a rinse reagent while the NA remains bound to the filter. Typically, the wash reagents have some amount of salt which still promotes the binding of the NA to the filter, while allowing removal of non-target materials. Next, the filter is eluted to remove the NA targets. In some embodiments, the elution is performed with a pH neutral buffer or basic buffer fluid. The target NA is then delivered to an attached reaction vessel to perform nucleic acid amplification.

In Workflow C, the fluid sample is exposed to sample treatment and/or chemically lyse the targets. Next, the NA freed by chemical lysing is bound to the filter. This step may utilize precipitating and binding reagent. Next, the filter is washed with a rinse reagent while the NA remains bound to the filter. Typically, the wash reagents have some amount of salt which still promotes the binding of the NA to the filter, while allowing removal of non-target materials. Next, the targets captured in the filter are heat and/or mechanically lysed. This may utilize sonication, and may further utilize glass beads to facilitate mechanical lysing of select targets. Then, the lysed target NA is eluted from the filter. In some embodiments, the elution is performed with a pH neutral buffer or basic buffer fluid. The target NA is then delivered to an attached reaction vessel to perform nucleic acid amplification. Thus, in this workflow, the workflow allows for lysing of multiple differing targets, some requiring only chemically lysing (e.g. viral targets), and others requiring mechanical lysing (e.g. bacteria, spores, etc.), such that all these target NAs can be released from a single sample and tested by the same sample cartridge. While the above workflow described mechanical lysing after chemical lysing, it is appreciated that other workflows may be utilized in which chemical lysing occurs after mechanical lysing, while in other workflows, the chemical and mechanical lysing can occur concurrently.

In some embodiments, the sample cartridge includes an identifier with information as to the appropriate workflow needed for a particular panel of assays, so that an instrument module receiving the sample cartridge operates according to the specified workflow.

FIGS. 22A-23D show experimental results illustrating marked improvements in performance of the improved cartridge design, such as that shown in FIGS. 1 and 5A-5C, as compared to a conventional cartridge for testing virus and free DNA, such as that shown in FIGS. 11A-11D. In these experiments, the universal cartridge A+ and the conventional cartridge C were used to detect NATROL SARS-CoV-2 under testing conditions that used various fluidic flow rates within the cartridge. These methods were aimed at either lowering the time to result by reducing the sample preparation time or were aimed at processing higher sample volumes in order to improve the sensitivity of the test kits. Each cartridge contained lysis buffer, wash buffer, elution buffer, polyethylene glycol and three separate beads used for the detection of SARS-CoV-2. The cartridges were run on a GeneXpert 16 Module System. Prior experiments with this assay revealed that the maximum fluid volume that could be processed with cartridge C was 300 uL at which volume pressure aborts (100 psi or greater) occurred approximately 50% of the time, thus volumes in cartridge C were reduced and limited to 125 uL to avoid pressure aborts. Flow rates for these experiments were 10 uL per second for cartridge C and 100 uL per second for CartA+.

FIGS. 22A-22D demonstrate that the universal cartridge A+ allowed for markedly faster sample processing times than conventional cartridge C. The filtration process in cartridge A+ and cartridge C separated nucleic acids from mixtures of nasal/nasopharyngeal swabs, lysis buffer and polyethylene glycol. The attribute of the cartridge A+ that allowed for this process to be faster was related to the design of the valve assembly, the filter material, and the width and depth of the filter. The combination of these attributes allowed for faster flow rates over and through the filter while maintaining pressure and performance. This material gave the filter an advantage over other filtration methods by lowering sample processing times while maintaining assay sensitivity. As can be seen in the first two data sets in FIGS. 22A-22D, when preparing a 125 uL sample, the sample processing time for universal cartridge A+ was 2 min, 25 sec, while the sample processing time for conventional cartridge C was 4 min, 8 sec. Thus, cartridge A+ processed the same volume as cartridge C in about half the time and with about half the pressure as obtained with cartridge C. As can also be seen, the universal cartridge A+ has similarly reduced sample processing times for 300 uL and 500 uL samples, while maintaining pressures that are similar to that seen cartridge C when processing 125 uL sample.

FIGS. 23A-23D demonstrate that the universal cartridge A+ design allows for processing of higher sample volumes resulting in higher sensitivity than conventional cartridge C design. The filtration process in this cartridge separated nucleic acids from mixtures of nasal/nasopharyngeal swabs, lysis buffer and polyethylene glycol. The attribute of the cartridge A+ that allowed for the processing of higher volumes was related to the valve assembly design and the filter material, including the width and depth of the filter. Flow rates are limited by pressure in both cartridges, but the configuration of cartridge A+ allows for flow rates up to at least 100 uL per second while the flow rates on cartridge C are limited to about 10 uL per second thus, more total sample was able to be processed with cartridge A+ as compared to cartridge C in less time while maintaining viable pressures below 100 psi. This results in more target available for detection as evidenced by the lower CoV Ct and higher CoV EPF in cartridge A+ as compared to cartridge C. As mentioned above, the maximum allowable pressure for these cartridges is 100 psi. Data not shown for cartridge C has previously demonstrated that for assay sample volumes of 300 uL resulted in pressure aborts approximately 50% of the time for conventional cartridge C, halting sample processing. Cartridge A+ allows for higher sample volumes (e.g. 300 uL, 700 uL and 1,000 uL) without reaching or exceeding the maximum pressure allowable (100 psi), as shown.

In the foregoing specification, the invention is described with reference to specific embodiments thereof, but those skilled in the art will recognize that the invention is not limited thereto. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art. Any references to publication, patents, or patent applications are incorporated herein by reference in their entirety for all purposes.

What is claimed is:

1. A sample cartridge for processing and/or analytical testing of a biological fluid sample, the sample cartridge comprising:
a cartridge body having a plurality of chambers therein, wherein at least one chamber is configured to receive a fluid sample;
a lysing chamber having a fluid inlet and a fluid outlet; and
a filter disposed within the lysing chamber, the lysing chamber further comprising,
a valve body; and
a valve cap,
wherein the valve body interfaces with the valve cap to define the lysing chamber therebetween,
wherein the filter is held within the lysing chamber secured between the valve body and the valve cap, and
wherein the valve body comprises the fluid outlet from the lysing chamber, and the valve cap comprises the fluid inlet into the lysing chamber;
wherein the filter is formed of glass fibers to facilitate affinity binding with free nucleic acids, and wherein the filter has a pore size selected to accommodate correspondingly sized glass beads to facilitate mechanical lysing.

2. The sample cartridge of claim 1, wherein the cartridge includes a plurality of glass beads in a chamber of the plurality, the glass beads correspondingly sized to the pore size of the filter.

3. The sample cartridge of claim 1, wherein the pore size is between 0.2 um and 2 um.

4. The sample cartridge of claim 1, wherein the pore size is about 0.7 um.

5. The sample cartridge of claim 1, further comprising:
a syringe that is movable to facilitate fluid flow into and from the lysing chamber by fluctuation of pressure.

6. The sample cartridge of claim 1, wherein the valve cap is configured such that a gap between the cap and the filter is 0.003" or greater.

7. The sample cartridge of claim 1, wherein the valve cap and the valve body are configured so that a fluid flow path therebetween is without any 90 degree corners so as to inhibit any buffer carryover along the fluid flow path.

8. The sample cartridge of claim 1, wherein the cap and/or the valve body include one or more support protrusions extending into the lysing chamber adjacent the fluid inlet and/or the fluid outlet so as to facilitate consistent and uniform flow of fluid sample through the lysing chamber for chemical lysing and/or infill of lysing agents across the filter to facilitate mechanical lysing.

9. The sample cartridge of claim 8, wherein the one or more protrusions comprise oval-shaped posts.

10. The sample cartridge of claim 1, wherein the valve cap comprises at least a pair of protrusions or posts extending into the lysing chamber adjacent the fluid inlet to press the filter away from the fluid inlet to facilitate improved infill of glass beads into the lysing chamber.

11. The sample cartridge of claim 10, wherein the valve body comprises at least a pair of protrusions or posts extending into the lysing chamber adjacent the fluid outlet to press the filter away from the fluid outlet to facilitate improved fluid flow and reduce stress on the filter.

12. The sample cartridge of claim 1, wherein the valve body comprises at least a pair of protrusions or posts extending into the lysing chamber adjacent the fluid outlet to press the filter away from the fluid outlet to facilitate improved fluid flow and reduce stress on the filter.

* * * * *